(12) United States Patent
Houde-Walter et al.

(10) Patent No.: US 10,495,413 B2
(45) Date of Patent: Dec. 3, 2019

(54) THERMAL MARKING SYSTEMS AND METHODS OF CONTROL

(71) Applicant: LMD Power of Light Corp., Rochester, NY (US)

(72) Inventors: Susan Houde-Walter, Rush, NY (US); William R. Houde-Walter, Rush, NY (US); Daniel J. Balonek, Bergen, NY (US); Brian L. Olmsted, Spencerport, NY (US); Michael W. Allen, Shortsville, NY (US)

(73) Assignee: LMD Power of Light Corporation, Rochester, NY (US)

( * ) Notice: Subject to any disclaimer, the term of this patent is extended or adjusted under 35 U.S.C. 154(b) by 0 days.

(21) Appl. No.: 15/789,591

(22) Filed: Oct. 20, 2017

(65) Prior Publication Data
US 2018/0216914 A1 Aug. 2, 2018

Related U.S. Application Data

(63) Continuation of application No. 15/243,545, filed on Aug. 22, 2016, now Pat. No. 9,797,682, which is a (Continued)

(51) Int. Cl.
| | |
|---|---|
| *F41G 1/36* | (2006.01) |
| *F41G 3/14* | (2006.01) |
| *H04N 5/33* | (2006.01) |
| *G01J 5/10* | (2006.01) |
| *G01N 21/47* | (2006.01) |

(52) U.S. Cl.
CPC .............. *F41G 1/36* (2013.01); *F41G 3/145* (2013.01); *G01J 5/10* (2013.01); *H04N 5/33* (2013.01); *G01N 21/47* (2013.01)

(58) Field of Classification Search
CPC ... F41G 1/36; F41G 3/145; G01J 5/10; G01N 21/47; H04N 5/33
See application file for complete search history.

(56) References Cited

U.S. PATENT DOCUMENTS

| | | |
|---|---|---|
| 4,713,544 A | 12/1987 | Grage |
| 4,737,028 A | 4/1988 | Smith |

(Continued)

OTHER PUBLICATIONS

S, Hugger et al., "Spectral beam combining of quantum cascade lasers in an external cavity," SPIE Digital Library; Dec. 14, 2010; pp. 73250H-1 thru 73250H-7; vol. 7325.

(Continued)

*Primary Examiner* — Mark R Gaworecki
(74) *Attorney, Agent, or Firm* — Lee & Hayes, P.C.

(57) ABSTRACT

A target marking system includes a light source configured to emit a beam of thermal radiation and to impinge the beam onto a target. The system also includes a detector configured to collect radiation passing from the target to the detector along a path. The radiation passing from the target in response to impingement of the beam onto the target. The system further includes an optics assembly disposed optically upstream of the detector along the path. The optics assembly includes at least one of an afocal power changer, a camera objective, a catadioptric lens, and a zoom system configured to condition the radiation passing from the target to the detector.

20 Claims, 14 Drawing Sheets

Related U.S. Application Data continuation of application No. 14/571,269, filed on Dec. 15, 2014, now Pat. No. 9,423,214, which is a continuation of application No. 13/405,914, filed on Feb. 27, 2012, now Pat. No. 8,912,492, which is a continuation-in-part of application No. 13/359,069, filed on Jan. 26, 2012, now abandoned, which is a continuation-in-part of application No. 13/271,924, filed on Oct. 12, 2011, now Pat. No. 9,062,932.

(60) Provisional application No. 61/392,697, filed on Oct. 13, 2010.

(56) References Cited

U.S. PATENT DOCUMENTS

| | | | |
|---|---|---|---|
| 5,064,988 A | | 11/1991 | E'nama et al. |
| 5,214,532 A | | 5/1993 | Hall et al. |
| 5,843,143 A | * | 12/1998 | Whitehurst ............ A61N 5/062 607/88 |
| 5,933,272 A | | 8/1999 | Hall |
| 6,351,478 B1 | | 2/2002 | Heberle |
| 6,362,872 B1 | | 3/2002 | Berdanier |
| 7,054,339 B1 | | 5/2006 | Hu et al. |
| 7,316,262 B1 | | 1/2008 | Rini et al. |
| 7,535,936 B2 | | 5/2009 | Day et al. |
| 7,564,567 B2 | | 7/2009 | Chen et al. |
| 7,573,921 B2 | | 8/2009 | Yumoto et al. |
| 7,732,767 B2 | | 6/2010 | Houde-Walter |
| 7,961,906 B2 | | 6/2011 | Ruedin |
| 8,049,966 B2 | | 11/2011 | Chann et al. |
| 8,912,492 B2 | | 12/2014 | Houde-Walter et al. |
| 2001/0046385 A1 | * | 11/2001 | Salapow ............ H04N 5/2251 396/429 |
| 2003/0174315 A1 | | 9/2003 | Byren et al. |
| 2004/0027564 A1 | * | 2/2004 | Some .................... G01N 21/47 356/237.5 |
| 2005/0006590 A1 | * | 1/2005 | Harrison .................. G01J 3/02 250/372 |
| 2005/0054943 A1 | | 3/2005 | Baum et al. |
| 2005/0280906 A1 | * | 12/2005 | Scheiner ................ G02B 17/06 359/726 |
| 2006/0013270 A1 | | 1/2006 | Yumoto et al. |
| 2006/0088271 A1 | | 4/2006 | Ghoshal |
| 2007/0030865 A1 | | 2/2007 | Day et al. |
| 2008/0304524 A1 | | 12/2008 | Marsland, Jr. et al. |
| 2009/0110019 A1 | | 4/2009 | Houde-Walter et al. |
| 2009/0224153 A1 | | 9/2009 | Houde-Walter |
| 2010/0229448 A1 | | 9/2010 | Houde-Walter et al. |
| 2011/0002585 A1 | | 1/2011 | Gibson et al. |
| 2011/0080311 A1 | | 4/2011 | Pushkarsky et al. |
| 2011/0103412 A1 | | 5/2011 | Patel et al. |
| 2011/0103414 A1 | | 5/2011 | Day et al. |
| 2011/0173870 A1 | | 7/2011 | Day et al. |
| 2011/0216792 A1 | | 9/2011 | Chann et al. |
| 2011/0222566 A1 | | 9/2011 | Weida et al. |
| 2012/0033697 A1 | | 2/2012 | Goyal et al. |
| 2012/0119112 A1 | | 5/2012 | Houde-Walter et al. |
| 2012/0154598 A1 | | 6/2012 | Houde-Walter et al. |
| 2014/0097747 A1 | | 4/2014 | Bader |
| 2015/0097967 A1 | | 4/2015 | Houde-Walter et al. |
| 2015/0292836 A1 | | 10/2015 | Houde-Walter et al. |
| 2016/0010951 A1 | | 1/2016 | Houde-Walter et al. |
| 2016/0370145 A1 | | 12/2016 | Houde-Walter et al. |
| 2017/0234650 A1 | | 8/2017 | Houde-Walter et al. |

OTHER PUBLICATIONS

Shankar Krishnan et al., "A Novel Hybrid Heat Sink Using Phase Change Materials for Transient Thermal Management of Electronics," IEEE Transactions on Components and Packaging Technologies; Jun. 2, 2005; pp. 281-289; vol. 28, No. 2.

Office Action for U.S. Appl. No. 14/571,269, dated Jan. 30, 2015, Susan R. Houde-Walter, "Thermal Marking Systems and Methods of Control", 4 pages.

Office action for U.S. Appl. No. 12/831,907, dated Oct. 3, 2013, Houde-Walter, "Encoded Signal Detection and Display ", 10 pages.

Final Office Action for U.S. Appl. No. 12/831,907, dated Dec. 10, 2014, Susan Houde-Walter, "Encoded Signal Detection and Display", 8 pages.

Office action for U.S. Appl. No. 15/243,545, dated Dec. 2, 2016, Houde-Walter et al., "Thermal Marking Systems and Methods of Control", 4 pages.

Office action for U.S. Appl. No. 13/271,924, dated Dec. 30, 2013, Houde-Walter et al., "Thermal Marking Systems and Methods of Control", 9 pages.

Office action for U.S. Appl. No. 12/831,907, dated Apr. 8, 2014, Houde-Walter, "Encoded Signal Detection and Display", 8 pages.

Office Action for U.S. Appl. No. 12/831,907, dated Jun. 16, 2015, Susan Houde-Walter, "Encoded Signal Detection and Display", 8 pages.

Office Action for U.S. Appl. No. 13/359,069, dated Aug. 26, 2014, Susan Houde-Walter, "Thermal Marking Systems and Methods of Control", 8 pages.

Office action for U.S. Appl. No. 14/571,269, dated Sep. 1, 2015, Houde-Walter et al., "Thermal Marking Systems and Methods of Control", 10 pages.

Office action for U.S. Appl. No. 14/862,870, dated Nov. 16, 2015, Houde-Walter et al., "Thermal Marking Systems and Methods of Control", 6 pages.

V. Shatikian et al., "Numerical investigation of a PCM-based heat sink with internal fins," International Journal of Heat and Mass Transfer; 2005, pp. 3689-3706; vol. 48.

J. Wagner et al., "Infrared semiconductor lasers for DIRCM applications," Technology for Optical Countermeasures V; Dec. 14, 2010; pp. 71150A-1 thru 71150A-11; vol. 7115.

* cited by examiner

THERMAL MARKING SYSTEMS AND METHODS OF CONTROL

CROSS-REFERENCE TO RELATED APPLICATIONS

The present application is a continuation of U.S. patent application Ser. No. 15/243,545, filed Aug. 22, 2016, which is a continuation of U.S. patent application Ser. No. 14/571, 269, filed Dec. 15, 2014, now U.S. Pat. No. 9,423,214, which is a continuation of U.S. patent application Ser. No. 13/405,914, filed Feb. 27, 2012, now U.S. Pat. No. 8,912, 492, which is a continuation-in-part of U.S. patent application Ser. No. 13/359,069, filed Jan. 26, 2012, which is a continuation-in-part of U.S. patent application Ser. No. 13/271,924, filed Oct. 12, 2011, now U.S. Pat. No. 9,062, 932, which claims the benefit of U.S. Provisional Application No. 61/392,697, filed Oct. 13, 2010. The entire disclosures of each of these applications are incorporated herein by reference.

STATEMENT REGARDING FEDERALLY SPONSORED RESEARCH OR DEVELOPMENT

Not applicable.

REFERENCE TO A "SEQUENCE LISTING"

Not applicable.

BACKGROUND OF THE INVENTION

Field of the Invention

The present disclosure relates to systems and methods for marking a target, and in particular, to systems and methods for marking a target with thermal radiation.

Description of Related Art

In combat arenas, some target marking applications may require use of radiation, such as a thermal beam, to mark targets in a way that may not be detectable by the target. For example, since thermal beams are not visible with the naked eye or with common infrared viewers, a soldier or other user of a thermal target marking system may be able to identify and/or otherwise mark a potential target without the target being able to see, for example, a targeting dot on his person. However, use of thermal radiation to mark targets is not without its own inherent complications.

A quantum cascade laser ("QCL") may be utilized to emit thermal beams in such applications, however, because the beams emitted by QCLs are inherently divergent, employing a QCL in such applications typically requires additional componentry configured to shape the thermal beam. For example, known beam shaping techniques may be used to increase the resolution of the thermal beam, thereby allowing the beam to appear smaller when impinging upon the target. However, such shaping techniques typically reduce the intensity of the thermal beam. Thus, the resulting beam, although desirably narrower, may be difficult for thermal beam detectors to view at great distances. As a result, such marking systems may be undesirable for use by, for example, snipers or other medium to long-range combat applications.

In addition, QCLs are inherently inefficient as light sources. For example, most typical QCLs give off a great deal of heat relative to the amount of light produced when the QCL is provided with an electrical current or voltage. While this inherent inefficiency may not be terribly problematic in a laboratory or other environment in which power and cooling components can be adapted relatively easily for use with such QCLs, such inefficiencies make it much more difficult to utilize QCLs in, for example, hand-held target marking devices or other devices in which space, weight, mobility, and/or other parameters are much more tightly constrained.

For example, utilizing a QCL in a hand-held target marker typically requires the use of one or more portable power sources such as, for example, batteries or the like. Because such batteries are generally low energy power sources, and because such batteries may only be capable of providing power for a limited time, utilizing such batteries to power a relatively inefficient QCL can be problematic. For example, such batteries may be depleted relatively quickly due to the large power draw placed on them by the QCL. In addition, even when powered by such batteries, the QCL may give off substantial amounts of heat and may require one or more cooling components to be thermally connected thereto to optimize QCL performance. Such cooling components may represent an additional parasitic load on the batteries being utilized, and may further reduce the useful life of such batteries. Due to these difficulties, the use of QCLs in hand-held or other portable target marking devices has been limited.

The embodiments of the present disclosure are aimed at overcoming one or more of these deficiencies.

SUMMARY OF THE INVENTION

In an exemplary embodiment of the present disclosure, a target marking system includes a plurality of light sources, each light source of the plurality of light sources configured to generate a respective beam of thermal radiation, and an optics assembly configured to form an emitted beam from the respective beams and to direct the emitted beam toward the target.

In another exemplary embodiment of the present disclosure, a target marking system includes a light source generating a beam of thermal radiation and a cooling element thermally connected to the light source.

In a further exemplary embodiment of the present disclosure, a target marking system includes a plurality of light sources, each light source of the plurality of light sources configured to generate a respective beam of thermal radiation, and an optics assembly configured to form an emitted beam from the respective beams and to direct the emitted beam toward the target. The optics assembly includes a plurality of adjustment windows, each adjustment window of the plurality of adjustment windows enabling manual alignment of at least one of the respective beams of thermal radiation. For example, the adjustment windows may be moved in unison.

In a further exemplary embodiment of the present disclosure, a method of controlling a target marking system includes scanning a target with a detector tuned to detect thermal radiation, the detector comprising a pixel array and scanning sequentially along individual rows of the array, identifying an area of the target likely to be impinged upon by an emitted beam of the target marking system, and energizing a light source during a time period in which the detector scans along a row of the array corresponding to the identified area. The method also includes de-energizing the light source during a remaining time period in which the detector scans along one or more rows of the array not corresponding to the identified area.

In still another exemplary embodiment of the present disclosure, a method of controlling a target marking system, includes directing power to a quantum cascade laser with one of a buck converter, a flyback converter, a forward converter, a buck-boost converter, a single ended primary inductor converter, a two switch forward converter, a push-pull converter, a half bridge converter, and a full bridge converter. The method also includes generating a beam of thermal radiation with the quantum cascade laser in response to the power received.

In a further exemplary embodiment, a target marking system includes a light source configured to emit a beam of radiation, and a controller connected to the light source and configured to pulse the beam emitted by the light source. The controller includes a drive circuit comprising a first converter connected in series with a second converter, and a capacitor connected in series between the first and second converters. The target marking system also includes a power source connected to the light source via the drive circuit.

In another exemplary embodiment, a target marking system includes a light source configured to emit a beam of thermal radiation, an optics assembly receiving the beam and directing the beam to exit a housing of the target marking system, and a controller disposed within the housing and connected to the light source. The controller includes a drive circuit having a first converter connected in series with a second converter, and a capacitor connected in series between the first and second converters. The system also includes a power source connected to the light source via the drive circuit. The drive circuit provides a substantially constant current to the light source during pulsed operation of the light source.

In still another exemplary embodiment of the present disclosure, a method of controlling a target marking system includes directing a substantially constant current from a power source of the target marking system to a light source of the system via a drive circuit. The drive circuit includes a first converter connected in series with a second converter, and a capacitor connected in series between the first and second converters. The method also includes generating a pulsed beam of radiation with the light source in response to receipt of the substantially constant current.

In another exemplary embodiment of the present disclosure, a target marking system includes a light source configured to emit a beam of thermal radiation and to impinge the beam onto a target. The system also includes a detector including a plurality of pixels and at least one display component, the at least one display component being configured to assist in forming an image of the beam impinging the target. The detector is configured to collect radiation passing from the target to the detector along a path. The radiation passing from the target in response to the beam impinging the target. The system further includes an optics assembly disposed optically upstream of the detector along the path. The optics assembly includes at least one of an afocal power changer, a camera objective, a catadioptric lens, and a zoom system configured to condition the radiation passing from the target to the detector.

In yet another exemplary embodiment of the present disclosure, a target marking system includes a light source configured to emit a beam of thermal radiation and to impinge the beam onto a target. The system also includes a detector configured to collect radiation passing from the target to the detector, wherein the radiation passes from the target in response to the beam impinging the target, and the detector includes at least one lens. The system further includes an optics assembly configured to narrow a field of view of the detector, thereby magnifying the radiation passing from the target to the detector. The system using the magnified radiation to form an image of the beam impinging the target.

In a further exemplary embodiment of the present disclosure, a method of controlling a target marking system includes directing a beam of thermal radiation to impinge upon a target, and collecting radiation from the target, wherein the collected radiation passes from the target, along a path, in response to the beam impinging upon the target. The method also includes magnifying the collected radiation at a location along the path, and using the magnified radiation to form an image of the beam impinging the target.

DETAILED DESCRIPTION OF THE DRAWINGS

Figure 1:
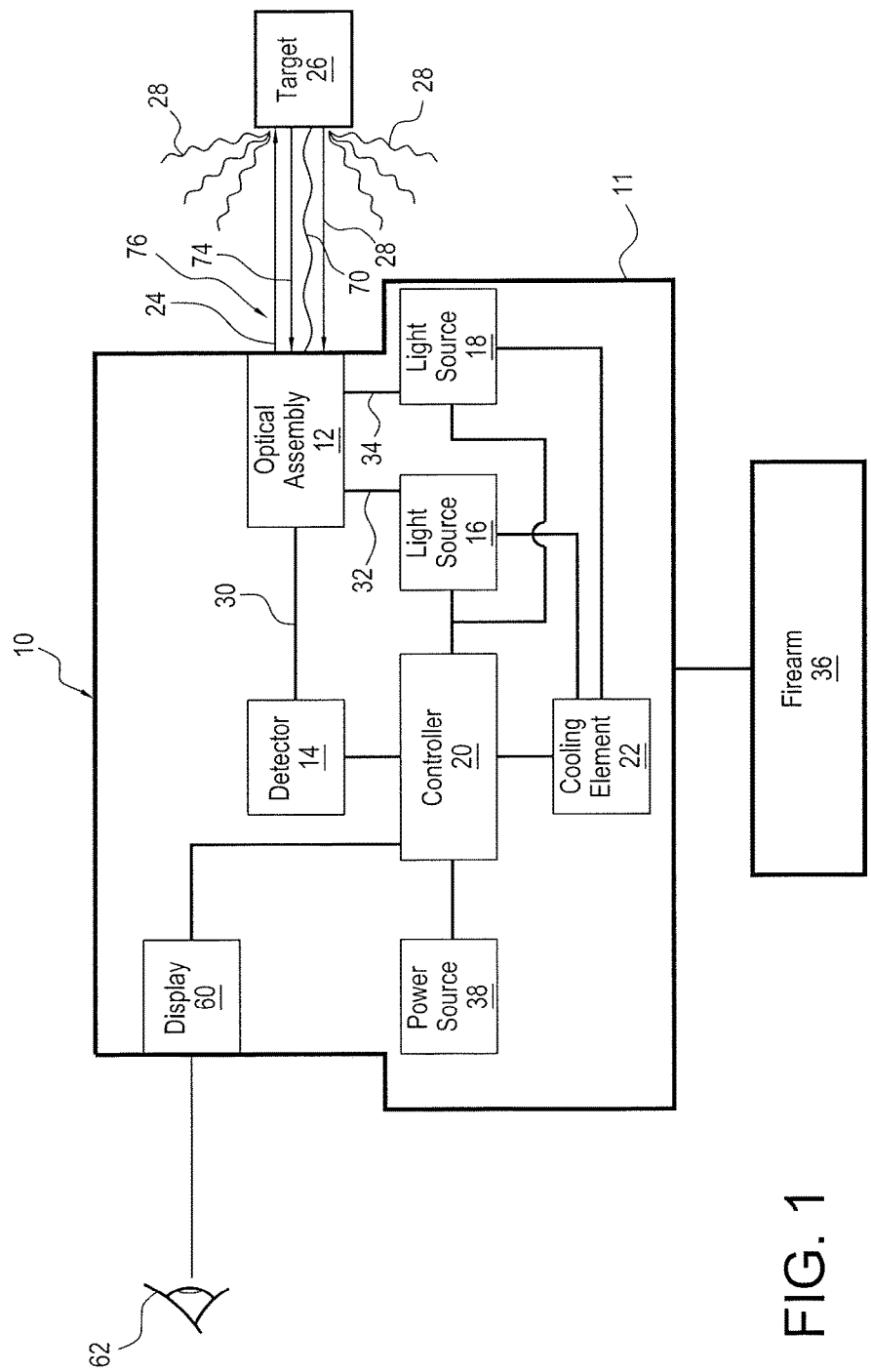
FIG. 1 is a schematic illustration of a target marking system according to an exemplary embodiment of the present disclosure.

FIG. 1 illustrates a target marking system 10 according to an exemplary embodiment of the present disclosure. As shown in FIG. 1, an exemplary system 10 may include, among other things, an optics assembly 12, a detector 14, and at least one light source 16. While exemplary embodiments of the system 10 may include a single light source 16, additional exemplary embodiments of the system 10 may include at least one additional light source 18. The detector 14 and the light sources 16, 18 may be optically, electrically, physically and/or otherwise connected to the optics assembly 12 in any known way. For example, the optical connection between the detector 14 and the optics assembly 12 may enable light and/or other forms of radiation to pass between the optics assembly 12 and the detector 14 along a beam path 30. In addition, the optical connection between the optics assembly 12 and the one or more light sources 16, 18 may enable light and/or other forms of radiation to pass between the optics assembly 12 and the light sources 16, 18 along respective beam paths 32, 34.

The target marking system 10 may further include, for example, a controller 20, a cooling element 22, and/or a power source 38. The controller 20 may be configured to control each of the components of the system 10, and the controller 20 may be electrically, and/or otherwise controllably connected to, for example, the detector 14, light sources 16, 18, cooling element 22, and/or power source 38 to facilitate such control. As will be described in greater detail below, the cooling element 22 may be thermally connected to at least one of the light sources 16, 18, and the power source 38 may be configured to provide power to the light sources 16, 18, controller 20, cooling element 22, detector 14, and/or other components of the target marking system 10. As shown in FIG. 1, the power source 38 may be electrically connected to one or more components of the target marking system 10 via the controller 20. In such an exemplary embodiment, the controller 20 may assist in distributing power from the power source 38 to the components of the system 10. Alternatively, one or more components of the system 10 may be directly connected to the power source 38.

The target marking system 10 may be configured for use in conjunction with and/or for removable connection to one or more handheld devices such as, for example, a firearm 36. Although not illustrated in FIG. 1, it is understood that the system 10 may further include one or more locking assemblies, clamping mechanisms, and/or other components configured to assist in removably attaching the system 10 to the firearm 36. Such locking assemblies or clamping mechanisms may enable the user to mount and/or otherwise connect the system 10 to any one of a plurality of commercially available mounts based on user preference. In an exemplary embodiment, the system 10 may be mounted on a Picatiny rail of the firearm 36. An additional exemplary embodiments, however, the system 10 may be connected to other known rails, such as, but not limited to dove tail rails and T-rails. In addition, the locking assembly and/or clamping mechanism may enable the system 10 to be easily removably attachable to other portions of the firearm 36 based on user preference or other ergonomic considerations.

The target marking system 10 may include a housing 11, and at least one of the first and second light sources 16, 18 may be disposed substantially within the housing 11. The housing 11 may define one or more orifices through which beams, pulses, signals, or other like radiation emitted from the light sources 16, 18 may exit the housing 11. In still another exemplary embodiment, the light sources 16, 18, optics assembly 12, and/or the detector 14 may be disposed substantially within the housing 11. In a further exemplary embodiment, each component of the system 10 may be disposed substantially within the housing 11 and, in such an exemplary embodiment, the system 10 may be a single-piece system removably connectable to the firearm 36.

Figure 12:
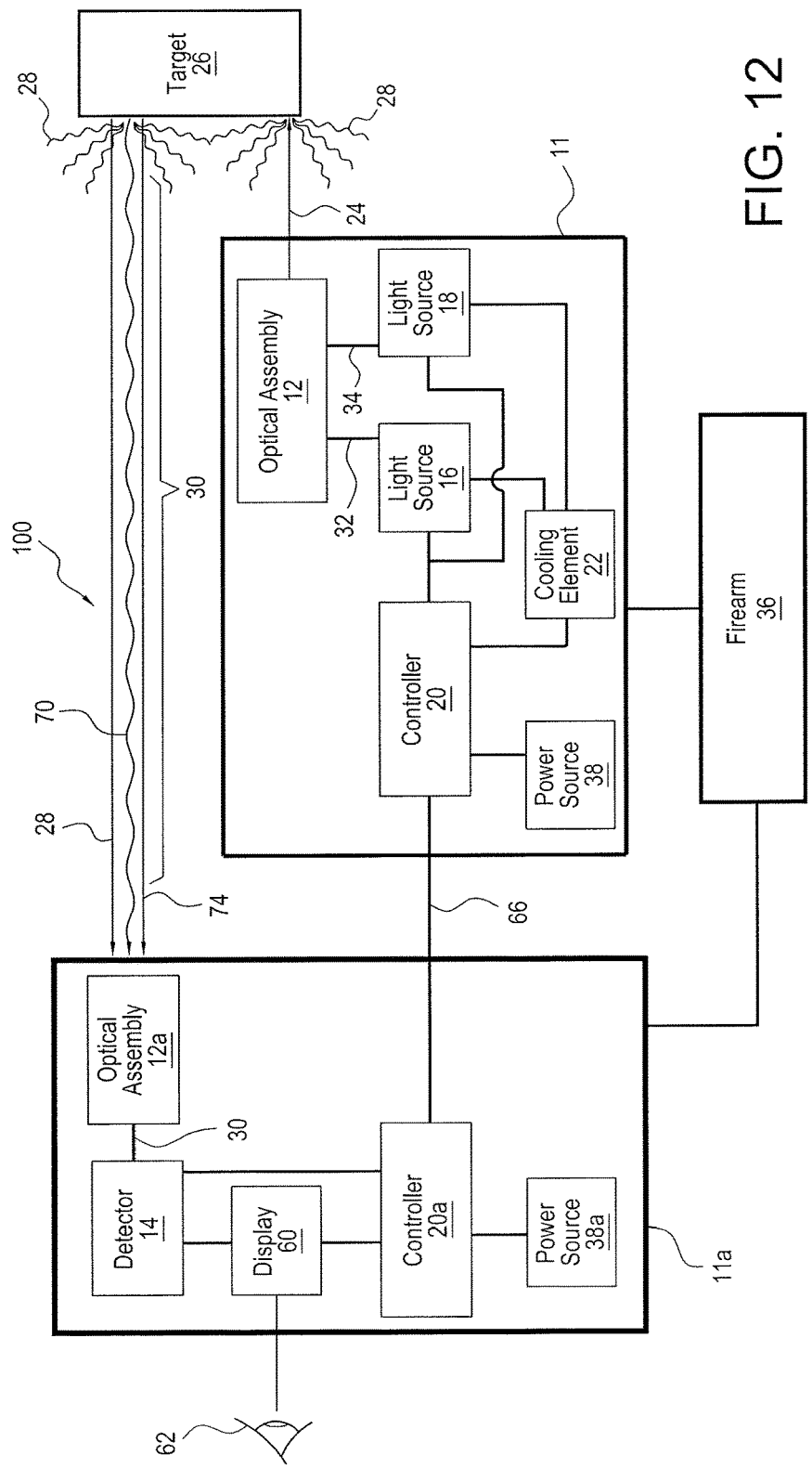
FIG. 12 is a schematic illustration of a target marking system according to another exemplary embodiment of the present disclosure.
Figure 14:
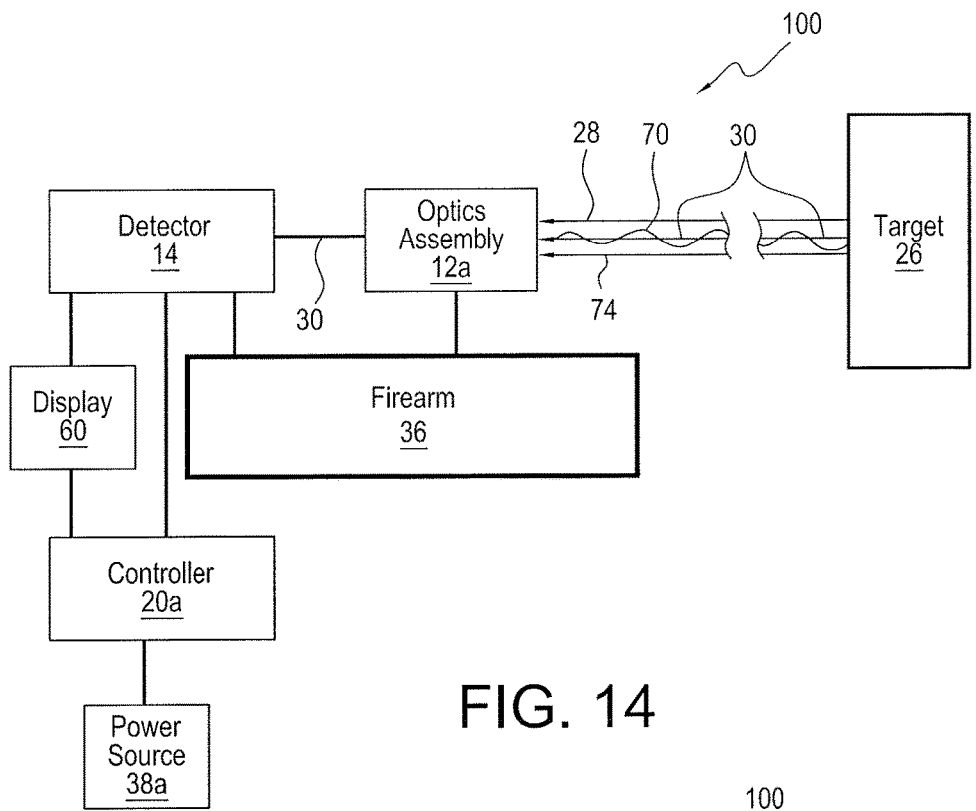
FIG. 14 is a partial schematic illustration of a target marking system according to a further exemplary embodiment of the present disclosure.
Figure 15:
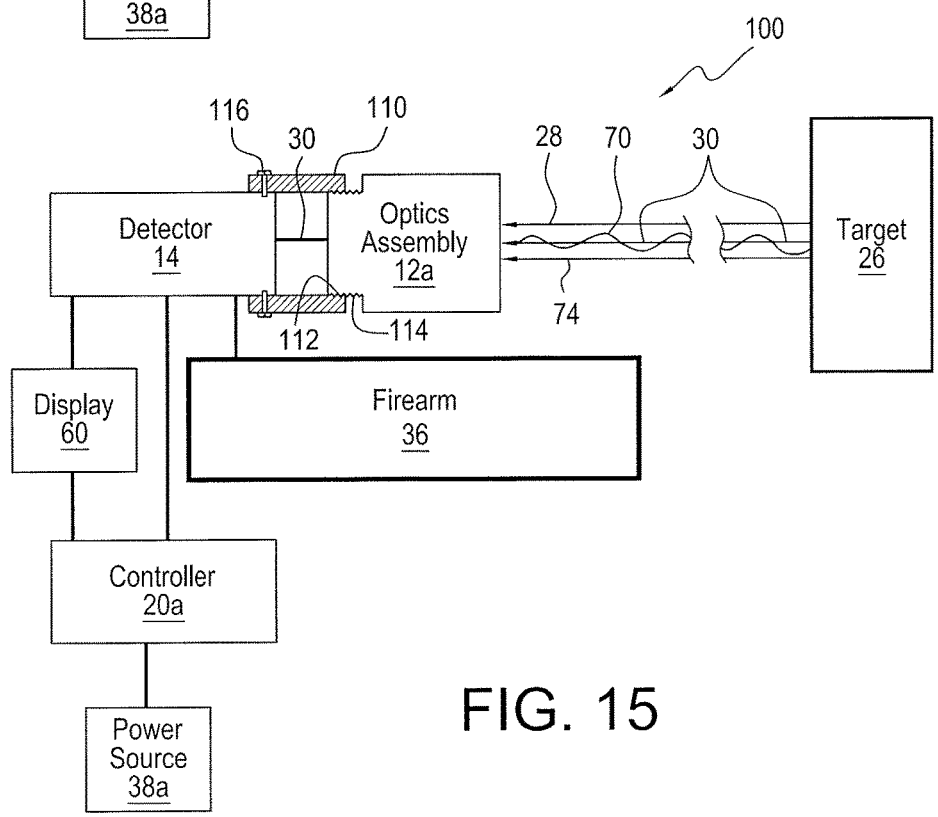
FIG. 15 is a partial schematic illustration of a target marking system according to still another exemplary embodiment of the present disclosure.

As shown in FIG. 12, in a further exemplary embodiment, a target marking system 100 may comprise at least two housings containing the components of the system 100. As shown in FIGS. 14 and 15, in still further exemplary embodiments, one or both of these housings may be omitted to facilitate connecting one or more components of the system 100 to each other and/or to the firearm 36. Wherever possible, like components of the systems 10, 100 are described herein using like item numbers. The exemplary system 100 may have a first housing 11 containing at least a portion of a first optics assembly 12, the light sources 16, 18, the controller 20, the cooling element 22, and the power source 38. The exemplary system 100 may also comprise a second housing 11*a* containing at least a portion of a second optics assembly 12*a*, a second controller 20*a*, and a second power source 38*a*. The second housing 11*a* may further include, for example, the detector 14 and the display 60 described herein. It is understood that, in an exemplary embodiment, the second housing 11*a*, second optics assembly 12*a*, second controller 20*a*, and second power source 38*a* may be substantially optically, structurally, functionally, and/or operably similar to the respective housing 11, optics assembly 12, controller 20, and power source 38 described herein. In addition, although one or more elements of the above components may be disposed in separate housings 11, 11*a*, it is understood that together, these separate elements may comprise a single component of the system 100. For example, although the first optics assembly 12 may be disposed within the first housing 11 and the second optics assembly 12*a* may be disposed within the second housing 11*a*, in an exemplary embodiment, the first and second optics assemblies 12, 12*a* may comprise a single optics assembly of the system 100. Likewise, although the first controller 20 may be disposed within the first housing 11 and the second controller 20*a* may be disposed within the second housing 11*a*, in an exemplary embodiment, the first and second controllers 20, 20*a* may comprise a single controller of the system 100.

As shown schematically in FIG. 12, the first and second housings 11, 11*a* may be removably attachable to the firearm 36 using any of the locking assemblies, clamping mechanisms, rails, and/or other components described herein. In addition, the first and second controllers 20, 20*a* may be electrically and/or operably connected via any connection 66 known in the art. Such a connection 66 may be made by wire, Bluetooth, RF, and/or other known connection means. Accordingly, information, data, signals, and/or control commands may be transmitted between the controllers 20, 20*a*, via the connection 66, to facilitate operation of one or more components of the system 100.

It is understood that any of the components, control strategies, connectors, circuit topographies, operations, functions, and/or other characteristics of the various embodiments described herein may be employed by either or both of the exemplary systems 10, 100 illustrated in FIGS. 1, 12, 14, and 15. However, for ease of description, the exemplary embodiment of the system 10 illustrated in FIG. 1 shall be described for the remainder of this disclosure unless otherwise specified. Light beams, pulses, signals, or other like radiation emitted from the light sources 16, 18 may exit the housing 11 and/or otherwise pass from the target marking system 10 along one or more respective emitted beam paths 76. Such emitted radiation 24 may impinge upon a target 26 and, depending upon the configuration of the target 26, such contact may result in the emission of radiation 28 from the target 26. This contact may also result in radiation 74 being rejected and/or otherwise reflected by the target 26, as well as radiation 70 being scattered by the target 26. Such re-emitted, reflected, and/or scattered radiation 28, 74, 70 may enter the housing 11 and/or the target marking system 10. For example, such radiation may be collected by the detector 14 via the optics assembly 12, 12*a*.

In an exemplary embodiment, the target 26 may direct such radiation 28, 74, 70 to pass through the same optics assembly 12 used to condition the radiation emitted by the light sources 16, 18. In such an embodiment, the radiation 28, 74, 70 may pass from the optics assembly 12 to the detector 14 along the beam path 30, and the optics assembly 12 may be disposed optically upstream of the detector 14 along the path 30. It is understood that such radiation 28, 74, 70 may pass from the target 26 in response to impingement of the beam of radiation 24 onto the target 26. It is also understood that the beam path 30 may extend from the target 26 to the detector 14. Such a beam path 30 is shown schematically in FIGS. 1, 12, 14, and 15. In this way, the target marking system 10 may utilize a single optics assembly 12 to condition the beams, pulses, signals, or other radiation 24 emitted from the light sources 16, 18, to condition re-emitted, reflected, and/or scattered radiation 28, 74, 70 directed to the optics assembly 12 by the target 26, and to direct such radiation 28, 74, 70 to the detector 14. Since the same optics assembly 12 is employed by the light sources 16, 18 and the detector 14, the target marking system 10 of the present disclosure may be significantly smaller, lighter, less complicated, less expensive, and easier to calibrate than marking systems utilizing discrete optics assemblies for the light sources and the detector associated therewith. However, as shown in FIGS. 12, 14, and 15, in additional exemplary embodiments, a target marking system 100 may employ a second optics assembly 12*a* to condition such radiation 28, 74, 70.

Referring again to FIG. 1, the light sources 16, 18 may comprise, for example, any of a variety of lasers. Typically, the light sources 16, 18 are self-contained, and one or more of the light sources 16, 18 may include one or more dedicated lenses separate from the optics assembly 12. The light sources 16, 18, may comprise, for example, any combination of a green laser, a red laser, a QCL, a super continuum laser, an infrared laser, an infrared light emitting diode ("LED"), a white and colored LED, a laser having an output of approximately 5 mW (it is understood that lasers having an output greater than approximately 5 mW or less than approximately 5 mW may also be used), an interband cascade laser ("ICL"), and a short wavelength infrared laser ("SWIR"). It is understood that a SWIR may emit a signal, beam, pulse, and/or other radiation having a wavelength of between, approximately 0.9 μm and approximately 2.5 μm. It is also understood that a QCL may be selected to operate in substantially ambient temperature conditions while producing a beam, pulse, signal, and/or other radiation having a wavelength between approximately 2 μm and approximately 30 μm. For example, a QCL may emit a beam having a wavelength between approximately 2 μm and approximately 5 μm (mid-wave) or between approximately 8 μm and approximately 30 μm (long-wave). In a further exemplary embodiment, the light sources 16, 18 may each comprise QCLs, thereby providing for a target marking system 10 configured to produce and/or otherwise emit beams having a plurality of different useful wavelengths for marking and/or other known applications. For example, the system 10 may comprise a fusion imager or other such device configured to emit and/or detect radiation in more than one spectral band and/or having more than one wavelength. Such fusion imagers may be useful in, for example, both thermal marking and night vision applications. In still another exemplary embodiment, one or more of the light sources 16, 18 may comprise a carbon dioxide laser.

As shown in FIG. 1, any of the light sources 16, 18 employed by the target marking system 10 may be operably connected to an appropriate controller. The controller 20 may include an appropriate driver, control circuitry signal processor, transformers, inductors, capacitors, and/or any other control, boost, and/or drive components. Such a driver may be, for example, configured to assist in controllably operating the light sources 16, 18. In addition, such a signal processor may be configured to modify the gain, contrast, brightness, color, and/or other optical characteristics of an input signal received from the detector 14. Such an input signal may be representative of a change in resistivity and/or other thermal, mechanical, optical, or electrical characteristic of one or more components of the detector 14, and such components may be pixels thereof. Thus, the controller 20 may be configured to receive an input signal from the detector 14 and produce a digitally enhanced output signal in response to the input signal. The controller 20 may send the output signal to, for example, a liquid crystal display, an organic light emitting diode, or any other like display 60. Alternatively, in additional exemplary embodiments, the detector 14 may be configured to produce such a digitally enhanced output signal, and direct such a signal to the controller 20 and/or the display 60.

The controller 20 and its components may be configured to operate at least one of the light sources 16, 18 in either pulsed or continuous modes of operation. Such components may include, one or more pulse generators, encoders, amplifiers, pulse switchers, and/or other known controller components. The controller 20 may control the light sources 16, 18 to emit radiation at any of the desirable wavelengths described herein. In addition, the controller 20 may control the light sources 16, 18 to emit radiation at a desired pattern or frequency. Such encoding or other temporal modulation of the radiation emitted by the light sources 16, 18 may be accomplished by any known means such as, but not limited to, modulating the current and/or voltage supplied to the light sources 16, 18, or by passing the radiation emitted by the light sources 16, 18 through an electro-optic, electro-acoustic, or other known modulator prior to permitting the radiation to exit the target marking system 10.

For example, the controller 20 may control the light sources 16, 18 to emit a beam having a predetermined frequency signature. Such a frequency signature may be repeated at predetermined intervals as desired. Alternatively, the controller 20 may control the light sources 16, 18 to emit one or more beams having a specified predetermined frequency pattern for as long as the beam is emitted. It is understood that such periodic frequency signatures or unique specified frequency patterns may be randomly generated as is typical in known encoding applications. Such controllers 20 may also be configured to communicate with, for example, controllers of other target marking system, or with other hardware utilized in combat arenas, in order to synchronize the functionality of the respective light sources 16, 18 utilized in a particular target marking application. Thus, the controller 20 may enable the signature of the beam, pulse, signal, and/or other radiation emitted by the light sources 16, 18 to be preset, and for the signature, wavelength, frequency, pulse pattern, and/or other characteristics of the emitted beam to be easily tunable in the field and/or during use.

The housing 11 of the target marking system 10 may be, for example, substantially fluid tight, such that the light sources 16, 18, controller 20, and/or other components of the system 10 may be operable in wet conditions. In an exemplary embodiment, the system 10 may be rated for substantially complete submersion in a liquid for a period of a least 30 minutes. In such an exemplary embodiment, the liquid may comprise, for example, fresh water or salt water. The system 10 may also be configured to withstand a substantial level of shock, vibration, and/or other contact typical of rugged use. For example, the system 10 may be configured for use in harsh environments such as, for example, jungles, swamps, deserts, rocky terrain, and/or other law enforcement, combat, or self-defense environments.

Although not illustrated in FIG. 1, it is understood that the target marking system 10 may also include at least one selection device configured to enable the user to select which of the light sources 16, 18 to utilize for a particular application. Such an exemplary selection device may comprise a button, rotatable knob, and/or other operator interface configured to select one or more of the light sources 16, 18 for use.

Although not shown in FIG. 1, the target marking system 10 may further include an activation device to enable the user to activate one or more of the light sources 16, 18 during use. Such an activation device may have a configuration similar to a trigger or a depressible switch. In such an exemplary embodiment, the activation device may be configured to energize and/or otherwise activate one or more of the light sources 16, 18 in either a pulsed mode, a continuous mode, and/or other mode selected by the user. It is understood that the activation device and/or the selection device may enable use of more than one light source 16, 18 at the same time.

The power source 38 may be any source of power known in the art such as, for example, one or more batteries. In an exemplary embodiment, the power source 38 may comprise a plurality of AA or CR-123 batteries. The power source 38 may be, for example, disposable and/or rechargeable, and the power source 38 may be configured to supply power to one or more lasers, QCLs, and or other light sources 16, 18 of the type described above. As described above, the power source 38 may be operably connected to the controller 20, the light sources 16, 18, the detector 14, the cooling element 22, and/or any of the other target marking system components described herein. In additional exemplary embodiments, the power source 38 may comprise N-type batteries, and/or lithium-manganese dioxide batteries. Although FIG. 1 illustrates the power source 38 being disposed within the housing 11, in additional exemplary embodiments, the power source 38 may be disposed outside of the housing 11. In an exemplary embodiment, the power source 38 may disposed on and/or otherwise mounted to the firearm 36 to which the target marking system 10 is connected.

In an exemplary embodiment in which at least one of the light sources 16, 18, comprises a QCL, a cooling element 22 may be disposed in thermal contact with the QCL. Such a cooling element may be disposed within the housing 11 and, in additional exemplary embodiments, such cooling elements may be disposed outside of the housing 11 such as, for example, on a portion of the firearm 36 to which the target marking system 10 is connected. In any of the embodiments described herein, a portion of the cooling element 22 may be exposed to ambient conditions. Regardless of its location, the cooling element 22 may be employed to maintain one or more of the light sources 16, 18 described herein at a desirable operating temperature. Certain configurations of the cooling element 22 may require, for example, energy input. Thus, in an exemplary embodiment, at least a portion of the cooling element 22 may be operably connected to the power source 38 and/or the controller 20.

The cooling element 22 may assist in cooling the QCL to a specified and/or desired operating temperature range. Additionally, the cooling element 22 may assist in cooling, for example, at least a portion of the housing 11 to a specified and/or desired operating temperature range. Such a portion of the housing 11 may include an internal compartment of the housing 11 and/or any desirable portion thereof. For example, the cooling element 22 may assist in cooling the QCL and/or a portion of the housing 11 to approximately room temperature, or between approximately 65 degrees Fahrenheit and approximately 75 degrees Fahrenheit. For example, the cooling element 22 may be either a passive device or an active device. Exemplary passive cooling elements 22 may include, for example, heat sinks, phase change elements, thermal conductors, heat pipes, radiators, and/or one or more fins configured to dissipate thermally energy from the QCL. In an exemplary embodiment, one or more components of the cooling element may be made from highly thermal conductive materials such as thermal pyroelectric graphite, or the like.

Active cooling elements 22, on the other hand, may include thermal electric coolers, Peltier modules, Sterling devices, and/or any other like cooling elements or devices known in the art. It is understood that in additional exemplary embodiments, the cooling element 22 may be omitted even if one or more QCLs are employed.

It is understood that the firearm 36 may comprise any light, medium, or heavy weapon system, including any hand gun, rifle, or other automatic or semi-automatic weapon known in the art. Such firearms 36 may be utilized in, for example, combat, law enforcement, self-defense, or other like applications. The target 26 illustrated in FIG. 1 may comprise any object at which the firearm 36 may be aimed and/or fired or otherwise discharged. Such targets may be animate objects, such as humans or animals, or inanimate objects, such as, for example, automobiles, security structures, or other objects typically targeted in the applications described herein.

The detector 14 may be any device or combination of devices configured to receive beams, pulses, signals, and/or other like radiation emitted, scattered, reflected, and/or otherwise directed by a target 26 and to interpret characteristics of the received radiation on a pixel-by-pixel basis. For example, the detector 14 may comprise a focal plane array such as, for example, a microbolometer array, or other like device having an array of pixels. Such a microbolometer array may be cooled or uncooled depending on the desired application. In an additional exemplary embodiment, the detector 14 may comprise a readout integrated circuit or other like component configured to detect a temporally modulated thermal input and produce an enhanced digital output signal based on the detected thermal input. In an exemplary embodiment, the readout integrated circuit may comprise at least a portion of the detector 14 and/or the controller 20.

In an exemplary embodiment, radiation received by the detector 14 such as, for example, re-emitted, reflected, and/or scattered radiation 28, 74, 70 passing from the target 26 to the detector 14 may impinge upon the detector 14, thereby heating a portion of the detector 14 and changing the electrical resistance of the heated portion. This resistance change may be measured and processed by, for example, the controller 20 and/or the readout integrated circuit. For example, pixels of the detector array may be heat sensitive, and may exhibit a change in resistance when light having a wavelength between approximately 8 μm and approximately 20 μm or longer is incident thereon. This re-emitted, reflected, and/or scattered radiation 28, 74, 70 may be utilized to create an image of, for example, the portion or area 92 (FIG. 11) of the target 26 impinged upon by the radiation beam 24 emitted by the target marking system 10. The image of the area 92 may be shown on the display 60 so as to be viewable by a user 62. For example, the display 60 may form a visual image in response to receiving a signal from the detector 14 and/or the controller 20, and the image may include a visual representation of the area 92 of the target, as well as visual representation of the beam 24 impinging the target 26.

Thus, the detector 14 may comprise a thermal sensor having an array 96 (FIG. 11) of pixels that can be controlled to look for, seek, identify, and/or otherwise detect radiation having a known, encoded, predetermined, and/or otherwise specified temporal modulation pattern. In further exemplary embodiments, the array 96 and/or the detector 14 may include one or more pixels. The detector 14 may be configured to identify such a pattern and code pixels in its array 96, on a pixel-by-pixel basis, based on the detected pattern. In exemplary embodiments, the plurality of pixels of the detector 14 may form, resolve, and/or otherwise represent, for example, the area 92 of the target 26 impinged upon by the beam 24. In such embodiments, greater than one pixel but less than each pixel of the plurality of pixels may represent the beam 24 impinging the target 26 such that the beam 24 can be identified, resolved, and/or otherwise distinguished from the target 26 by the user 62 in an image formed by the system 10. The detector 14 may send an input signal to the controller 20 or other components of the readout integrated circuit for processing. The input signal may include information indicative of the resistance of each pixel of the detector 14 over time. Such information may include, for example, the intensity level detected by each pixel over time. The controller 20 or other components of the readout integrated circuit may send an output signal to the display 60 indicative of and/or otherwise corresponding to the input signal. In an exemplary embodiment, the output signal may control the display 60 to modify the gain, contrast, brightness, color, and/or other characteristics of corresponding pixels of the display 60. It is understood that, in additional exemplary embodiments, such signals may be sent from the detector 14 to the display 60 directly.

The display 60 may illustrate the modulation detected by the detector 14 in any manner that is easily identifiable by the user 62, regardless of the environment in which the system 10 is used. For example, the display 60 may comprise a pixel array corresponding to the pixel array of the detector 14. The pixel array of the display 60 may be configured to display a thermal image of the target 26. The pixels of the display 60 displaying the portion or area of the target 26 impinged upon by the thermal beam 24 from the target marking system 10 may illustrate the point of impact of the beam 24 using, for example, red, green, yellow, orange, or other colors. Such pixel-by-pixel color-coding may enable the user 62 to easily identify the point of impact when looking at the display 60. Alternatively, one or more pixels of the display 60 may blink, flash, or otherwise temporally modulate in any known easily identifiable way. As will be described in greater detail below, one or more pixels of the display 60 may be controlled according to one or more corresponding pixels of the detector 14. The detector 14 may further include additional display components to facilitate the pixel coding and target image display described herein. For example, in addition to the pixels of the array 96 described above, the detector 14 may include at least one lens, window, filter, and/or other known optical component to assist in forming an image of the beam 24 impinging the target 26. Such lenses, pixels, and/or other additional components may be components of the detector 14, and such components may be separate from the various optics assemblies 12, 12a described herein.

In still further exemplary embodiments, the display 60 may include a selectively engageable "outline mode". When the outline mode of the display 60 is engaged, such as, for example, by one or more switches, buttons, or other like operator interfaces associated with the display 60 and/or the controller 20, the image shown on the display 60 may include only a perimeter corresponding to each respective object disposed within a field of view of the detector 14. Such a field of view will be described in greater detail below. In such embodiments, each perimeter of the one or more objects shown in the image may be defined by differences in levels of radiation emitted by each respective object. For example, the display 60 may define each respective perimeter along a two or three-dimensional interface of varying radiation levels and/or emissions. In such an outline mode, for example, a target 26 emitting relatively more or relatively less radiation than a background object will be represented by only an outline of the target 26 defined along a perimeter of the target 26. Likewise, a beam of radiation 24 impinging upon the target 26 may be characterized by a different level of radiation than the target 26. Thus, a perimeter of such a beam of radiation 24 may be shown in the image as being superimposed on and/or within a perimeter of the target 26.

The light sources 16, 18 may be controlled to emit radiation having a predetermined and/or specified temporal modulation pattern or signature, and such patterns or signatures may include periodic modulations or specified frequency patterns. The detector 14 may be controlled to identify any such temporal modulation patterns substantially instantaneously. In addition, such temporal modulation patterns can be rapidly and easily changed, using the controller 20 or other components of the systems 10 described herein, for operational security purposes. Such changes may occur, for example, during combat operations to reduce or eliminate the risk of enemy forces detecting the emitted, re-emitted, reflected, and/or scattered radiation 76, 28, 74, 70 discussed herein.

Thus, the components of the detector 14 may be controlled to seek, identify and/or look for, on a pixel-by-pixel basis, radiation having one of the predetermined and/or specified temporal modulation patterns discussed above using a gating process, a phase locking process, and/or other known processes. In such a gating process, the controller 20 may communicate to the detector 14 that a beam, signal, pulse, and/or other radiation has been emitted by the target marking system 10. In response, the detector 14 may attempt to locate and/or identify re-emitted, reflected, and/or scattered radiation 28, 74, 70 passing from the target 26, on a pixel-by-pixel basis, for a fixed period of time. Such gating processes may be initiated and/or otherwise effected due to a direct electrical connection between, for example, the controller 20 and the detector 14. Alternatively, such gating processes may be initiated and/or otherwise effected upon receipt of a wireless signal and/or trigger. Such a wireless signal may be, for example, a blue tooth and/or other like signal, and at least one of the controller 20 and the detector 14 may be configured to receive such a signal for effecting a gating process.

In a phase locking process, on the other hand, the detector 14 may be controlled to identify re-emitted, reflected, and/or scattered radiation 28, 74, 70 passing from the target 26 having a predetermined and/or specified temporal modulation pattern without being notified that the target marking system 10 has emitted a beam, signal, pulse, and/or other radiation. Instead, the detector 14 may detect and/or process all radiation passing thereto, and may determine whether any of the incoming radiation exhibits, for example, the predetermined and/or specified temporal modulation pattern, or other identifiable characteristics. If the incoming radiation does exhibit such a pattern or characteristic, the display 60 may be controlled to display, for example, a thermal image of the target 26 with the impact point of the thermal beam emitted by the target marking system 10 being color-coded in the image. It is understood that the gating, phase locking, and/or other like processes described herein may be employed on a pixel-by-pixel basis in embodiments of the detector 14 having pixel arrays or other like components. Moreover, the gating, phase locking, and/or other like processes described herein may be performed without performing the beam shaping processes described herein.

With continued reference to FIG. 1, the optics assembly 12 may comprise one or more optical components such as, for example, one or more lenses, windows, beam splitters, mirrors, prisms, beam combiners, diffraction gratings, and/or other known optical components configured to direct, condition, shape and/or otherwise control the passage of radiation therethrough. For example, the optics assembly 12 may be configured to collect as much re-emitted, reflected, and/or scattered radiation 28, 74, 70 as possible and to direct the collected radiation 28, 74, 70 to the detector 14. Such radiation may include, for example, any beams, pulses, signals, and/or other radiation emitted by the light sources 16, 18 in the thermal and/or other spectral band, as well as the re-emitted, reflected, and/or scattered radiation 28, 74, 70 received from the target 26. As described above, the target marking system 10 may comprise a single optics assembly 12 that is shared by the light sources 16, 18 and the detector 14. The optics assembly 12 may include, for example, one or more lenses, apertures, filters, modulators, and/or other optical components to facilitate the beam shaping techniques described herein. The optics assembly 12 may be, for example, an afocal power changer, a camera objective, a catadioptric lens, or any other known light collection system. In an additional exemplary embodiment, the optics assembly 12 may comprise any known zoom system. As described above with respect to FIGS. 1 and 12, the re-emitted, reflected, and/or scattered radiation 28, 74, 70 may pass from the target 26 to the detector 14 along the path 30. As shown in FIGS. 1 and 12, the optics assembly 12, 12a may be, for example, disposed optically upstream of the detector 14 along the path 30.

In the exemplary embodiments described herein, the optics assembly 12 may be configured to narrow and/or otherwise reduce a field of view of the detector 14, thereby magnifying the radiation 28, 74, 70 passing from the target 26 to the detector 14. The magnified radiation 28, 74, 70 may be used by, for example, the detector 14 and/or other components of the system 10 to form an image of the beam 24 impinging the target 26. In exemplary embodiments, the "field of view" of the detector 14 may be defined as the area from which radiation may pass to the detector 14. In such exemplary embodiments, the field of view may be two-dimensional or three-dimensional, and may be conical, cylindrical, circular, ovular, and/or any other known shape. By reducing the field of view of the detector 14, the optics assembly 12 may permit less radiation 28, 74, 70 to pass to the detector 14. Such a reduction in the field of view may, thus, increase the resolution of the detector 14, the display 60, and/or other components of the systems 10, 100 described herein. For example, in exemplary embodiments in which the display 60 forms a visual image of the area 92 of the target 26, the optics assembly 12 may increase the resolution of the visual representation of the beam 24 shown in the image. As a result of this increase in resolution, the user may be able to more easily see, identify, and/or distinguish the beam 24 from the target 26 when looking at the image on the display 60. For example, the optics assembly 12 may magnify the radiation 28, 74, 70 passing from the target 26 to the detector 14 at a location along the path 30. The optics assembly 12 may, for example, spread such magnified radiation 28, 74, 70 over the array 96 (FIG. 11) of pixels of the detector 14 such that the beam 24 can be seen more clearly. For example, the optics assembly 12 may spread the radiation 28, 74, 70 passing from the target 26 to the detector 14 over more than one pixel but over fewer than all of the pixels in the array 96 such that the beam 24 can be resolved from the target 26 in the resulting image. Due to the poor resolution characteristics of known target marking systems, it may be difficult for a user to see, identify, and/or distinguish a beam of radiation impinging a target, from the target itself, when looking at a display of the system. By imparting magnification (i.e., magnifying power) to the radiation 28, 74, 70 optically upstream of the detector 14, the optics assemblies 12, 12a of the present disclosure may assist in overcoming this deficiency. It is understood that in embodiments in which the optics assembly 12, 12a comprises a zoom system, the magnifying power may be adjustable.

As shown in one or more of FIGS. 1, 12, 14, and 15, the optics assembly 12, 12a may be disposed optically upstream of the detector 14, and separate from the detector 14, along the path 30, in any number of ways. For example, while FIGS. 1 and 12 illustrate embodiments in which the optics assembly 12, 12a may be disposed within a respective housing 11, 11a of the target marking system 10, 100, in further exemplary embodiments, the optics assembly 12, 12a may be connected directly or indirectly to the firearm 36 and/or to the detector 14. In such embodiments, one or both of the housings 11, 11a may be omitted. For example, as shown in FIG. 14, the optics assembly 12a and/or the detector 14 may be directly removably connected to the firearm 36. In such exemplary embodiments, the optics assembly 12a and/or the detector 14 may be removably connected to the firearm 36 via any of the locking assemblies, clamping mechanisms, and/or other components described above with respect to, for example, a rail of the firearm 36. In such an exemplary embodiment, the detector 14 and/or the optics assembly 12a may include separate respective housings, and the respective housing of the detector 14 and/or the optics assembly 12a may be removably connected to the firearm 36.

Alternatively, as shown in the exemplary embodiment of FIG. 15, the optics assembly 12a may be removably connected to the detector 14. In such an exemplary embodiment, the optics assembly 12a may be removably connected to the detector 14 optically upstream thereof, such as along the path 30 of the radiation 28, 74, 70 passing from the target 26 to the detector 14. In such embodiments, the target marking system 10, 100 may include a connector 110 removably connecting the optics assembly 12a and the detector 14.

The connector 110 may comprise any type of adapter, fitting, annular ring, releasable clamp, and/or other like connection device known in the art. Such connectors 110 may include one or more components sized, shaped, disposed, and/or otherwise configured to assist in removably coupling the optics assembly 12*a* and the detector 14. For example, the connector 110 may include a first component 112 removably connected to the optics assembly 12, and a second component 116 removably connected to the detector 14. The first and second components 112, 116 may be substantially structurally similar or, alternatively, the components 112, 116 may be structurally different. For example, as shown in FIG. 15, at least one of the first and second components 112, 116 may comprise threads or other like structures configured to mate with corresponding threads 114 of the optics assembly 12*a*. In another exemplary embodiment, at least one of the first and second components 112, 116 may comprise one or more set screws or other like structures configured to mate with a corresponding ridge, groove, shoulder, flange, indentation, hole, or other like structure of the detector 14. In further exemplary embodiments, at least one of the first and second components 112, 116 may comprise one or more clamps, clasps, fittings, spring-loaded connection devices, and/or other like structures configured to facilitate a releasable and/or otherwise removeable connection between the detector 14 and the optics assembly 12*a*.

As shown in FIG. 15, in exemplary embodiments, the connector 110 may be disposed at least partially between the detector 14 and the optics assembly 12*a*. In addition, at least one of the components 112, 116 may encircle a portion of at least one of the detector 14 and the optics assembly 12*a*. It is understood that the radiation 28, 74, 70 collected by the detector 14 may pass from the optics assembly 12*a* to the detector 14 via the connector 110 without being conditioned by the connector 110. Although the configuration of FIG. 15 illustrates the connector 110 removably connecting the detector 14 and the optics assembly 12*a* such that a space and/or gap is formed between the detector 14 and the optics assembly 12*a*, in further exemplary embodiments, the connector 110 may removably connect the detector and the optics assembly 12*a* such that the detector 14 abuts the optics assembly 12*a*. Moreover, in the exemplary embodiment of FIG. 15 the detector 14 and/or the optics assembly 12*a* may include separate respective housings, and the respective housing of the detector 14 and/or the optics assembly 12*a* may be removably connected via the connector 110. In still further exemplary embodiments, the optics assembly 12*a* and the detector 14 may be formed integrally together and/or may be permanently connected to one another. In such exemplary embodiments, the connector 110 may be modified to facilitate such permanent connection, or the connector 110 may be omitted.

Figure 2:
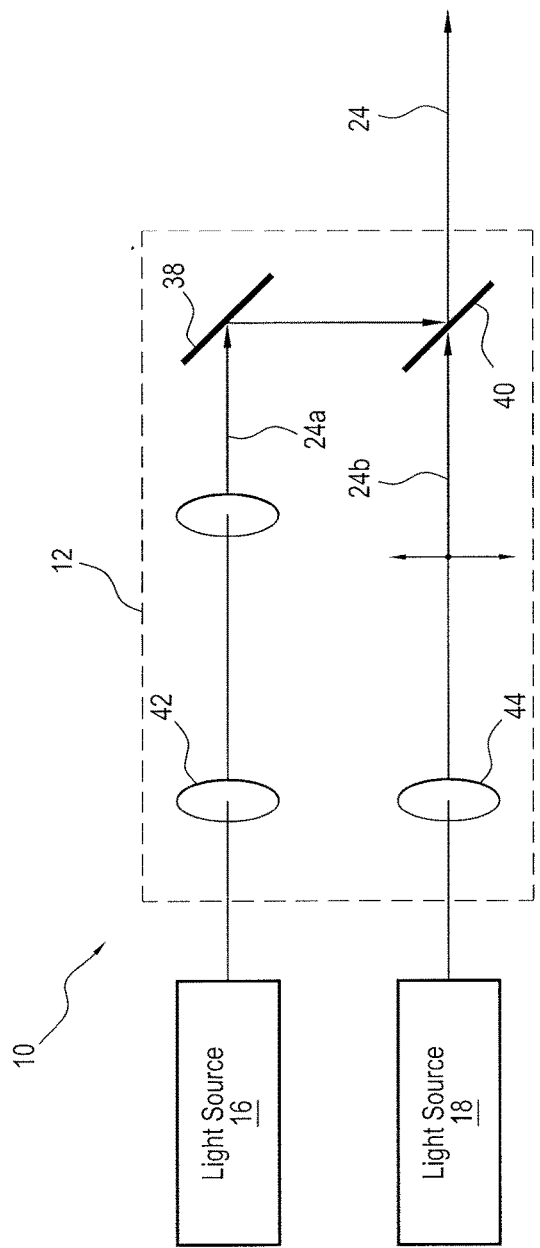
FIG. 2 is a partial schematic of a portion of an exemplary target marking system.

FIG. 2 illustrates an exemplary optics assembly 12 of the present disclosure. As shown in at least FIGS. 2-6, exemplary embodiments of the target marking systems 10, 100 described herein may employ multiple light sources 16, 18, 19 to form the emitted beam 24. The fusion and/or integration of multiple light sources in this way may assist in maximizing the total power, intensity, heat, energy, and/or other quantifiable metrics of the radiation directed to a target 26 by the target marking system 10, 100. In the embodiment shown in FIG. 2, a beam combiner 40 may be utilized to combine two orthogonal beams of radiation 24*a*, 24*b*. In such an exemplary embodiment, the beam combiner 40 may be, for example, a polarizing beam combiner such as, for example, a Brewster window or other like device. In an additional exemplary embodiment, the beam combiner 40 may comprise any known beam splitter. The beam combiner 40 may be configured to combine beams 24*a*, 24*b* having different polarities, regardless of wavelength, and to emit such beams 24*a*, 24*b* collinearly as a single emitted beam 24. Such an exemplary embodiment may be particularly useful in maximizing the power of the emitted beam 24 impinging upon a target 26 at relatively close distances.

As shown in FIG. 2, beam 24*a* emitted by the light source 16 may be linearly polarized such that the electrical field of the beam 24*a* is oriented in a direction substantially orthogonal to the path of the beam 24*a* (substantially into and substantially out of the page). The light source 18, on the other hand, may emit beam 24*b* characterized by an electrical field oriented in a direction substantially perpendicular to the path of the beam 24*b*. The beams 24*a*, 24*b* may pass through respective lenses 42, 44 disposed optically upstream of the beam combiner 40. The lenses 42, 44 may be, for example, any catadioptric lenses, refracting lenses, reflecting lenses, diffracting lenses, collimating lenses, and/or other lenses known in the art. Upon passing through the lens 42, the beam 24*a* may impinge upon a mirror 38 and/or other like optical component. The mirror 38 may direct the beam 24*a* onto the beam combiner 40. Alternatively, the light source 16 may be disposed at any desirable angle relative to the beam combiner 40 such that the beam 24*a* may be directed to impinge upon the beam combiner 40 without the use of a mirror 38. In such an exemplary embodiment, the mirror 38 may be omitted.

The light source 18 may direct the beam 24*b* onto the lens 44, and the lens 44 may direct the beam 24*b* to impinge upon the beam combiner 40. The different surface coatings, shapes, sizes, and/or other configurations of the beam combiner 40 may enable the beam combiner 40 to perform various desired beam combination functions. For example, the beam combiner 40 may be configured to reflect light and/or other forms of radiation having a first polarization and to transmit light and/or other forms of radiation having a second polarization. Such reflection and/or transmission functions may be performed by the beam combiner 40 regardless of the respective wavelengths of the various impinging beams. As shown in FIG. 2, the beam combiner 40 may reflect the beam 24*a* directed by the mirror 38 and having a first polarization. The beam combiner 40 may also transmit the beam 24*b* directed by the lens 44 and having a second polarization different from the polarization of beam 24*a*. In this way, the beam combiner 40 may emit beams 24*a*, 24*b* collinearly as the single emitted beam 24. The emitted beam 24 may be narrower, smaller in diameter, and/or more powerful than, for example, combined or overlapping non-collinear beams emitted by other exemplary target marking systems.

Figure 3:
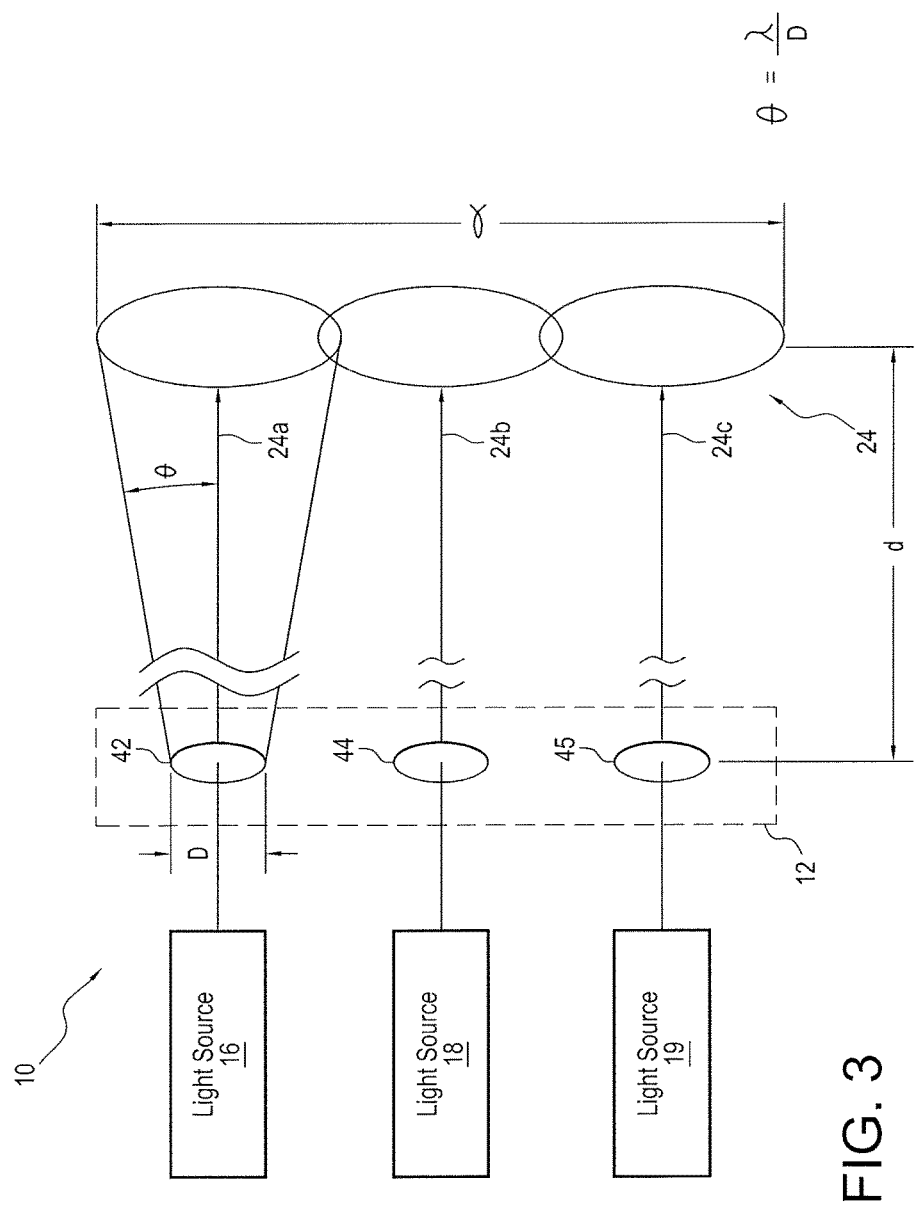
FIG. 3 is a partial schematic of a portion of another exemplary target marking system of the present disclosure.

FIG. 3 illustrates an exemplary embodiment in which a plurality of light sources 16, 18, 19 are employed to emit an emitted beam 24 that is made up of a combination of non-collinear beams 24*a*, 24*b*, 24*c*. It is understood that, in such an exemplary embodiment, any desired number of light sources may be employed, and in additional exemplary embodiments, two or more light sources may be used. In such exemplary embodiments, increasing the number of light sources utilized may result in an increase in the overall power, diameter, and/or other quantifiable optical characteristics of the resulting emitted beam 24. Thus, because such an exemplary embodiment may be scalable in nature, utilizing a plurality of light sources in the manner illustrated in FIG. 3 may be particularly advantageous for impinging the emitted beam 24 upon a target 26 disposed at relatively greater distances d as compared to the embodiment shown in FIG. 2. The exemplary embodiment of FIG. 3 may be particularly well suited in applications in which the overall diameter of the emitted beam 24 is less critical. For example, the exemplary configuration illustrated in FIG. 3 may be acceptable in applications in which an emitted beam 24 has a diameter that is approximately three times the size of a single beam 24a, 24b, 24c. As shown in FIG. 3, the overall diameter a of the emitted beam 24 may be slightly less than the sum of the diameters of the individual beams 24a, 24b, 24c in embodiments in which the beams 24a, 24b, 24c have some degree of overlap. The overall diameter a of the emitted beam 24 may be enlarged and/or reduced based on the spacing of the respective light sources 16, 18, 19.

As shown on FIG. 3, the respective beams 24a, 24b, 24c may be passed through one or more lenses 42, 44, 45, respectively. The lenses 42, 44, 45 may be structurally similar to the lenses 42, 44 described above with regard to FIG. 2. For example, the lenses 42, 44, 45 may be configured to collimate the respective beams 24a, 24b, 24c passing therethrough. Notwithstanding such collimation, each individual beam may exhibit a small degree of beam divergence represented by Θ in FIG. 3. In such an exemplary embodiment, the beam divergence Θ may be substantially equal to the wavelength λ of the respective beam 24a, 24b, 24c divided by the respective diameter D of the lens 42, 44, 45. As described herein, in exemplary embodiments, the wavelength of the individual beams 24a, 24b, 24c may be between approximately 2 μm and approximately 30 μm. In the exemplary embodiment shown in FIG. 3, the individual beams 24a, 24b, 24c may be combined regardless of wavelength or polarization. For example, the individual beams 24a, 24b, 24c may have the same wavelength, or at least one of the beams may have a wavelength different from the remaining beams. In addition, the individual beams 24a, 24b, 24c may have the same polarization, or at least one of the beams may have a different polarization than the remaining beams.

Figure 4:
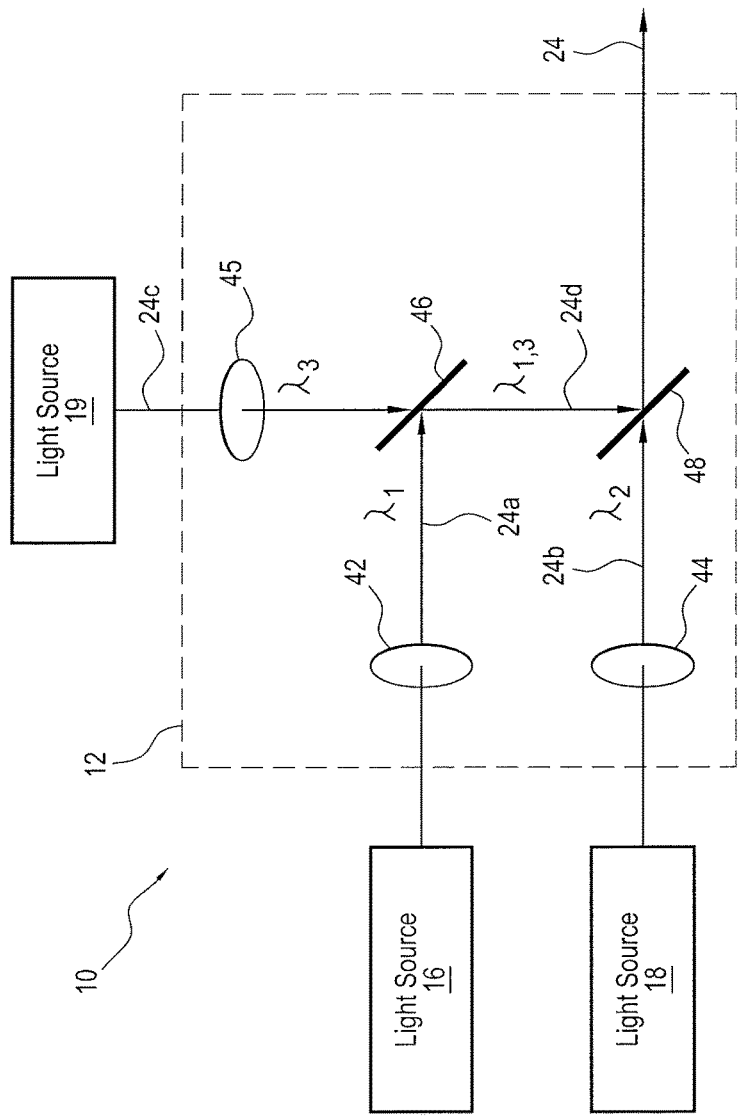
FIG. 4 is a partial schematic of a portion of still another exemplary target marking system of the present disclosure.

As shown in FIG. 4, in an additional exemplary embodiment, two or more individual beams having different wavelengths may be combined by exemplary optics assemblies 12 of the present disclosure, and such beams may have the same polarization or different polarizations. For example, individual beams 24a, 24b, 24c may be emitted by respective light sources 16, 18, 19, and passed through respective lenses 42, 44, 45. As described above, in an exemplary embodiment, the lenses 42, 44, 45 may assist in substantially collimating the individual beams 24a, 24b, 24c as they pass therethrough. In addition, each of the beams 24a, 24b, 24c may have different respective wavelengths, $\lambda_1$, $\lambda_2$, $\lambda_3$. In such an exemplary embodiment, two or more beams may be combined using one or more beam combiners and, as shown in exemplary FIG. 4, the first beam 24a having a first wavelength $\lambda_1$ may be combined with the third beam 24c having a wavelength $\lambda_3$ using a wavelength beam combiner 46. The wavelength beam combiner 46 may be configured to combine two or more beams of radiation such as, for example, light having different wavelengths, regardless of the polarization of the impinging beams. The thickness of the surface coatings and/or the number of surface coatings applied to the beam combiner 46 may be controlled and/or selected to reflect and/or transmit two or more beams in any desired way. For example, as shown in FIG. 4, the beam combiner 46 may be configured to transmit beams having a wavelength $\lambda_3$ and to reflect beams having a wavelength $\lambda_1$. As a result, when beam 24c impinges upon a first surface of the beam combiner 46 and beam 24a impinges on a second opposite surface of the beam combiner 46, the beam combiner 46 may emit a single substantially collinear beam including radiation characterized by both wavelengths $\lambda_1$ and $\lambda_3$. Such a beam 24d may then impinge upon a first surface of a second beam combiner 48. The beam combiner 48 may be, for example, substantially structurally similar to the beam combiner 46 described above. In such an exemplary embodiment, the beam combiner 48 may be configured to reflect radiation having wavelengths $\lambda_1$ and $\lambda_3$ and to transmit radiation having a wavelength $\lambda_2$. Accordingly, as shown in FIG. 4, the beam combiner 48 may permit the beam 24b having a wavelength $\lambda_2$ to pass therethrough, and may also reflect the beam 24d emitted by beam combiner 46. Accordingly, the beam combiner 48 may form an emitted beam 24 made up of beams 24d and 24b aligned substantially collinearly. The emitted beam 24 may include each of the wavelengths $\lambda_1$, $\lambda_2$, $\lambda_3$.

Figure 5:
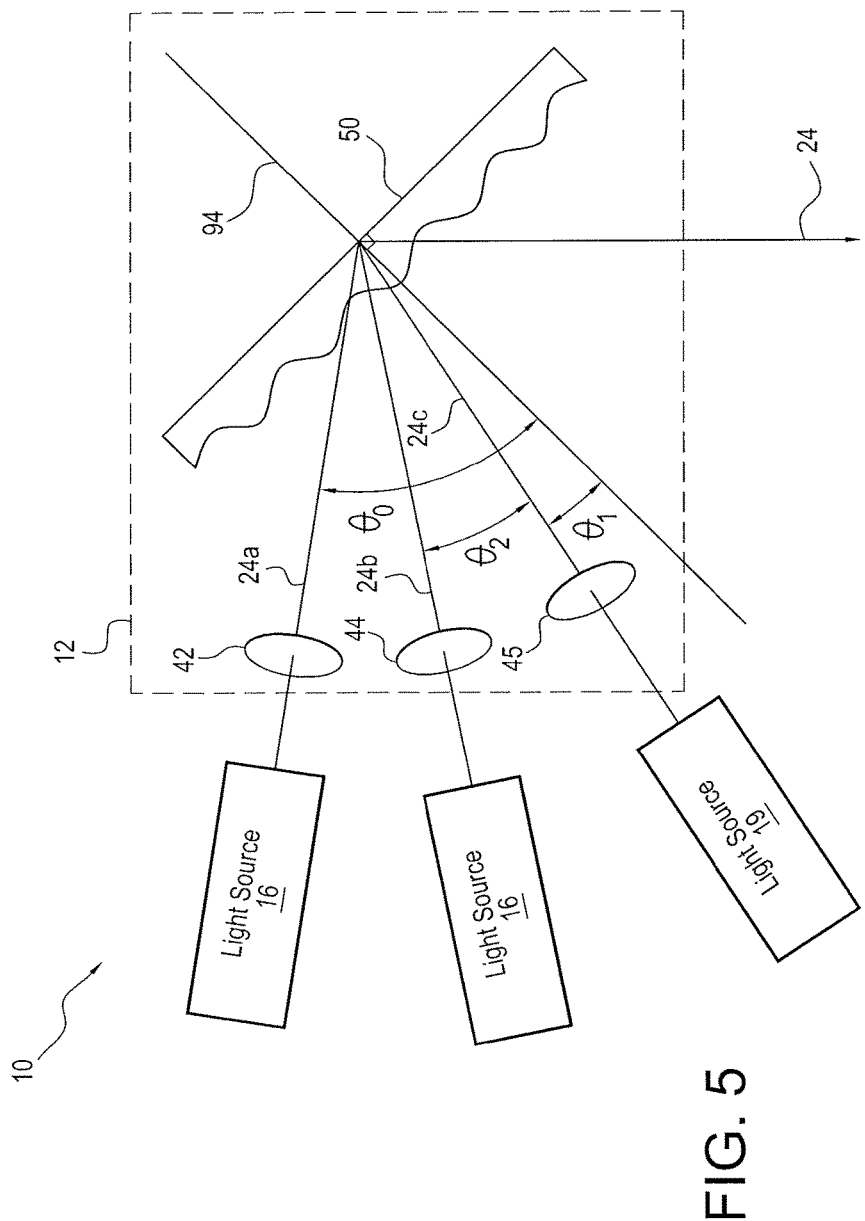
FIG. 5 is a partial schematic of a portion of yet another exemplary target marking system of the present disclosure.

In additional exemplary embodiments, individual beams from a plurality of light sources may also be combined utilizing one or more diffraction gratings or other like optical components. For example, as shown in FIG. 5, individual beams 24a, 24b, 24c may be emitted by respective light sources 16, 18, 19, and passed through respective lenses 42, 44, 45, as described above with regard to FIG. 4. However, instead of utilizing beam combiners 46, 48 to combine such individual beams, a diffraction grating 50 may be employed to form a single emitted beam 24. As described with regard to FIG. 4, each of the individual beams 24a, 24b, 24c may have the same polarization or different polarizations. In addition, each of the individual beams 24a, 24b, 24c may have the same or different wavelengths. Accordingly, the emitted beam 24 may include each of the wavelengths of the individual beams 24a, 24b, 24c. In addition, the individual beams 24a, 24b, 24c may be oriented and/or angled in any desirable way relative to a surface normal 94 of the diffraction grating 50. In addition, one or more lenses, windows, and/or other optical components may be employed by the exemplary optics assembly 12 illustrated in FIG. 5 to assist in orienting the individual beams 24a, 24b, 24c relative to one another such that a substantially collinear emitted beam 24 may be produced by the diffraction grating 50.

Figure 6:
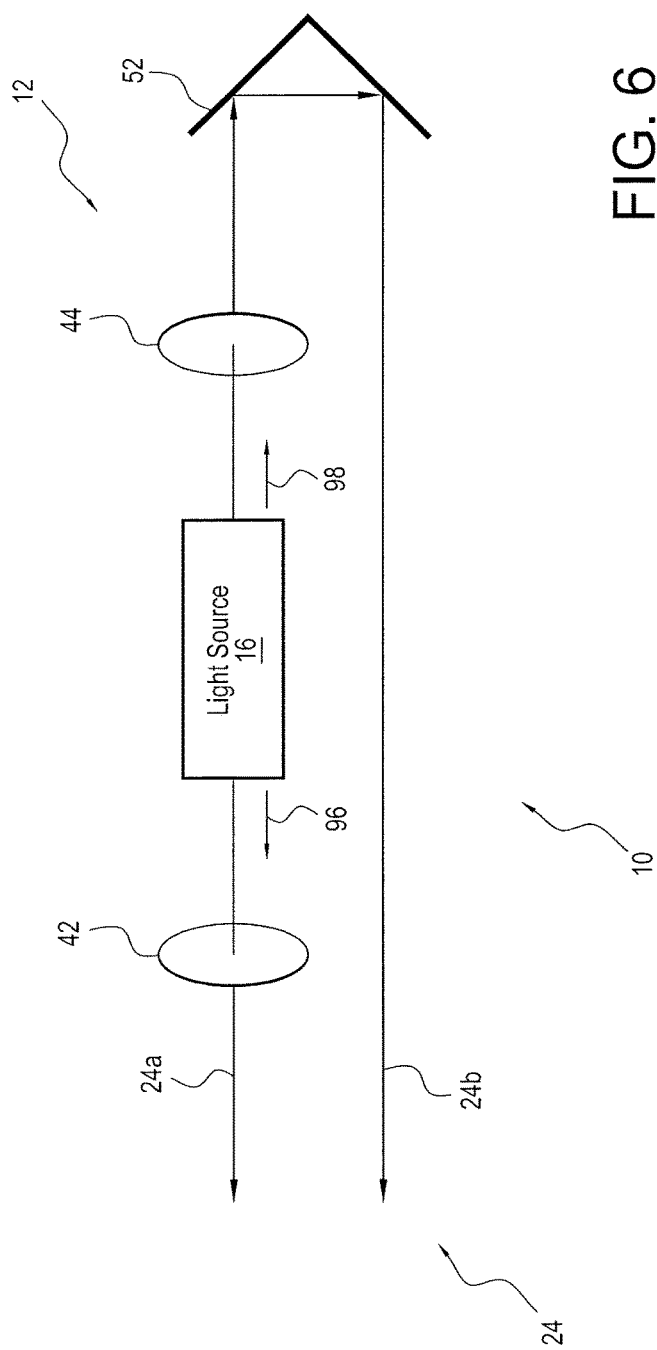
FIG. 6 is a partial schematic of a portion of a further exemplary target marking system of the present disclosure.

In still another exemplary embodiment, one or more optical components such as a prism, mirror, or the like may be utilized to capture, condition, redirect, and/or otherwise manipulate radiation emitted by one or more light sources of the type described herein. For example, as shown in FIG. 6, one or more of the light sources utilized by the systems 10, 100 may emit radiation in more than one direction. An exemplary light source 16 may emit a first individual beam 24a passing in a first direction shown by arrow 96, and a second individual beam 24b passing in a second opposite direction shown by arrow 98. Each of the beams 24a, 24b may be directed to pass through respective lenses 42, 44, and the beam 24b may impinge upon one or more mirrors or a prism 52 disclosed optically downstream of the lens 44. The prism 52 may redirect the beam 24b to be substantially parallel to the first beam 24a. In this way, the optics assembly 12 may be configured to maximize the amount of emitted radiation utilized by the system 10, 100. Such a configuration may result in an increase in the power, intensity, and/or other quantifiable characteristics of the emitted beam 24. In the exemplary embodiment of FIG. 6, the individual beams 24a, 24b may not be collinear upon passing from the optics assembly 12. However, the individual beams 24a, 24b may be substantially parallel to each other and may at least partially overlap. It is also understood that utilizing a prism 52 in the exemplary embodiment of FIG. 6 may assist in maintaining the parallel relationship of the individual beams 24a, 24b, and may reduce the complexity in manufacturing, for example, the optics assembly 12. For instance, because a prism 52 may be a substantially one-piece design, vibrations, agitations, and/or other movement of the optics assembly 12 may have very little effect on the parallel relationship between the beams 24a and 24b. On the other hand, replacing the prism 52 with one or more mirrors may make it more difficult to maintain, for example, a substantially parallel orientation between the individual beams 24a, 24b when the optics assembly 12 is shaken, jarred, vibrated, and/or otherwise moved. Such variations may occur due to relative movement between, for example, the one or more mirrors or the other optical components of the optics assembly 12 during use.

Exemplary embodiments of the present disclosure may also employ various thermal management schemes to account for the heat and other energy produced by the one or more light sources described herein. As discussed above, light sources such as QCLs and the like may give off a substantial amount of heat during operation. At the same time, such light sources may have an optimal operating temperature range within which efficiency is maximized. Accordingly, maximizing the efficiency of the systems 10, 100 described herein may require maintaining the one or more light sources 16, 18, 19 within their respective optimal operating temperature range. Accordingly, each of the light sources described herein may be thermally, physically, and/or otherwise operably connected to the cooling element 22 described above. In exemplary embodiments, the cooling element 22 may comprise one or more different active and/or passive cooling components configured to assist in removing heat from the respective light source to which it is connected. Removing heat in this way may be particularly advantageous when utilizing, for example, QCLs or other like light sources because as such light sources increase in temperature, these light sources become less efficient. Moreover, once a maximum operating temperature is exceeded, such light sources may cease to function. As described above, one or more active cooling elements 22 may be thermally connected to such light sources to assist in reducing the temperature thereof. However, such cooling elements 22 may require power in order to function. In addition, active cooling elements 22 may also produce heat during use. As a result, such active cooling components may not be suitable for use in all applications.

In additional exemplary embodiments, the cooling element 22 may be a passive device, and may include one or more passive cooling components thermally connected to the one or more light sources 16, 18, 19 to assist in removing heat therefrom. Such components may rely on, for example, diffusion to pull thermal energy away from the light sources 16, 18, 19, thereby cooling the respective light sources and optimizing their operational efficiency.

Figure 7:
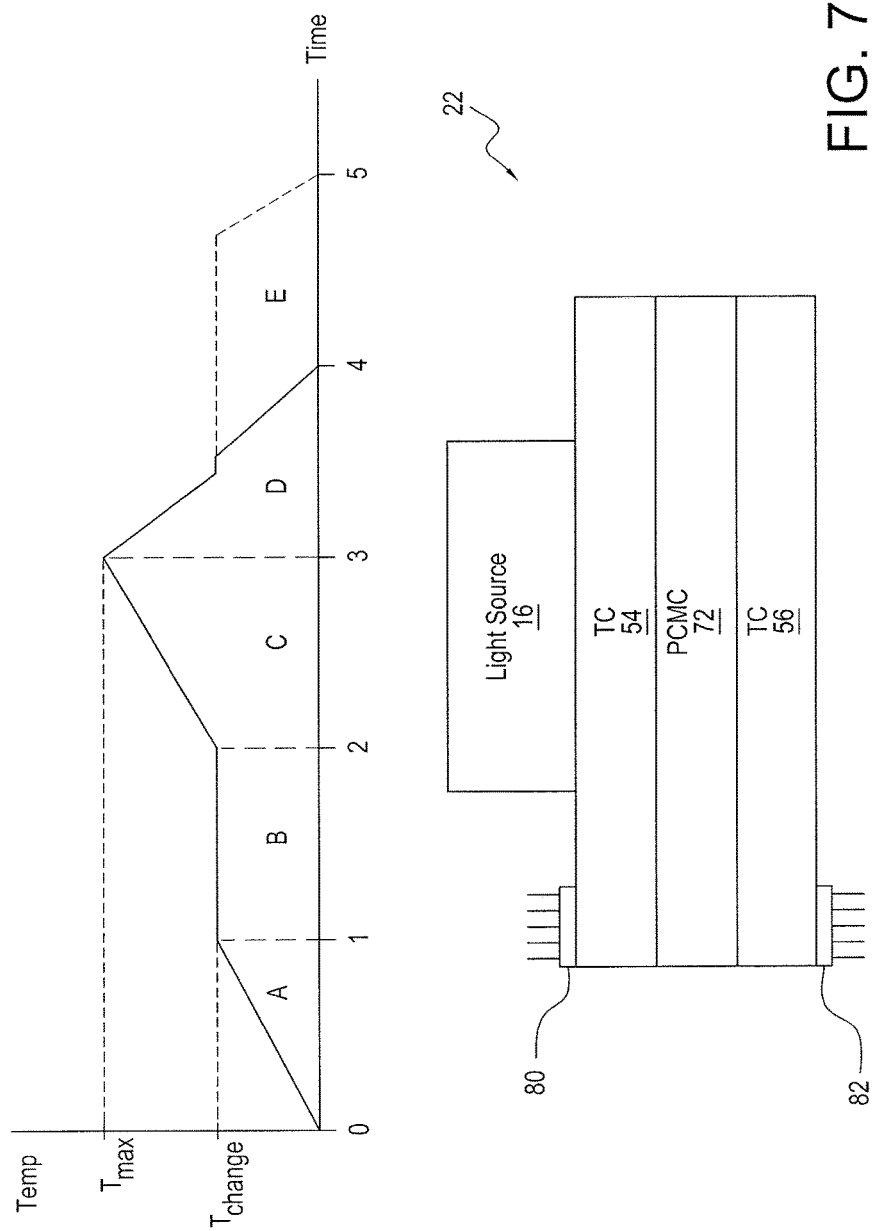
FIG. 7 illustrates a light source thermally connected to a cooling element according to an exemplary embodiment of the present disclosure.

As shown in FIG. 7, an exemplary cooling element 22 may include one or more thermal conductors 54, 56 thermally connected to a light source 16. The cooling element 22 may also include one or more components comprising phase change material or the like. Such a phase change material component 72 may also be thermally connected to light source 16. As shown in FIG. 7, in an exemplary embodiment, the phase change material component 72 may be thermally connected to the light source 16 via one or more of the thermal conductors 54, 56. Alternatively, the light source 16 may be directly connected and/or coupled to the phase change material component 72. The cooling element 22 may also include one or more additional cooling elements such as, for example, passive coolers 80, 82. Such passive coolers 80, 82 may be thermally connected to the respective thermal conductors 54, 56. Alternatively, such passive coolers 80, 82 may be directly connected and/or coupled to, for example, the light source 16 and/or the phase change material component 72. In additional exemplary embodiments, the passive coolers 80, 82 may be thermally connected to each other, and in further exemplary embodiments, the thermal conductors 54, 56 may be thermally connected to each other. It is understood that the passive coolers 80, 82 may comprise any of the heat sinks, radiators, fins, and/or other passive cooling components described above with regard to the cooling element 22. In addition, the thermal conductors 54, 56 may comprise any highly thermally conductive material known in the art such as, for example, copper, aluminum, titanium, and the like. In addition, one or more of the thermal conductors 54, 56 may comprise thermal pyroelectric graphite and/or other like materials. Such materials may be highly thermally conductive and may be utilized to enhance the thermal conductivity of one or more components of the cooling element 22. For example, at least one of the thermal conductors 54, 56 may be a highly thermally conductive plate or other like structure comprising an alloy formed by combining thermal pyroelectric graphite with copper.

As illustrated by the graph in FIG. 7, during operation the temperature of the light source 16 may increase from a substantially ambient temperature to a given operating temperature of the light source 16. Such an increase is illustrated in Section A of the graph. During this time, the light source 16 may dissipate heat to the first passive cooler 80 via the thermal conductor 54. The light source 16 may also dissipate heat to the phase change material component 72 via the thermal conductor 54, and as a result, the temperature of the phase change material component 72 may also rise. As illustrated in Section A of the graph, during continued operation, the temperature of the light source 16 may continue to rise and, during this time, the ability of the passive cooler 80 to dissipate the heat generated by the light source 16 may be exceeded. In such an exemplary embodiment, the phase change temperature ($T_{change}$) of the phase change material component 72 may be chosen and/or otherwise desirably selected such that the phase change material therein does not change phase until the amount of heat generated by the light source 16 exceeds the heat dissipation capabilities of the passive cooler 80. Once such a temperature ($T_{change}$) is reached, the phase change material within the phase change material component 72 may begin to change phase (for example, from solid to liquid). As shown by Section B of the graph illustrated in FIG. 7, during this phase change process the temperature of the light source 16 may remain substantially constant, and this constant temperature ($T_{change}$) may be maintained until such a phase change is completed. Once complete, the phase change material of the phase change material component 72 may no longer be capable of absorbing energy from the light source 16. In addition, the thermal energy stored/absorbed by the phase change material must be removed before the phase change material is capable of again absorbing heat. Accordingly, the thermal conductor 56 may be employed to transmit such stored thermal energy from the phase change material component 72 to the passive cooler 82, whereby such stored thermal energy can be properly dissipated. The passive coolers 80, 82 may be disposed within and/or external to the housing 11 of the assembly 10, 100 (FIG. 1, FIG. 12).

As shown in Section C of the graph illustrated in FIG. 7, while heat is being removed from the phase change material component 72, the temperature of the light source 16 may continue to rise until the maximum operating temperature ($T_{max}$) of the light source 16 is reached. Upon reaching this temperature, the light source 16 may no longer function, and may be deactivated in order to facilitate cooling thereof. Such a cooling phase may be represented by Section D of the graph illustrated in FIG. 7. In an exemplary embodiment, while the light source 16 is allowed to cool, one or more components of the cooling element 22 may again begin to dissipate and/or otherwise remove heat from the light source 16. As a result, the slope of the curve represented in Section D of the graph may be steeper than, for example, the slope of the curve in Section C between $T_{change}$ and $T_{max}$. Alternatively, the elevated temperature of one or more components of the cooling element 22 may extend the required cooling time of the light source 16 and/or may otherwise extend the time required to cool the light source 16. Such an exemplary extension of required cooling time is illustrated by Section E of the graph shown in FIG. 7. In an exemplary embodiment, once the phase change material component 72 reaches a state or temperature in which its phase change material is again capable of absorbing thermal energy, the phase change material component 72 may continue absorbing heat from the light source 16 and may again assist in maintaining the light source 16 at the temperature $T_{change}$ as shown in Section E.

In additional exemplary embodiments, it may be desirable and/or advantageous to dissipate and/or otherwise remove heat from one or more of the light sources described herein in a directional manner. For example, the size, shape, and/or other configurations of the housing 11 (FIG. 1, FIG. 12) and/or other packaging components may not allow for a direct physical connection between, for example, one or more of the light sources 16 and the various components of the cooling element 22. In such exemplary embodiments, the cooling element 22 may employ one or more components configured to remove thermal energy and/or other energy from the one or more light sources described herein and transmit such energy, in a directional manner, to the phase change material component 72, passive coolers 80, 82 and/or other components of the cooling element 22.

Figure 8:
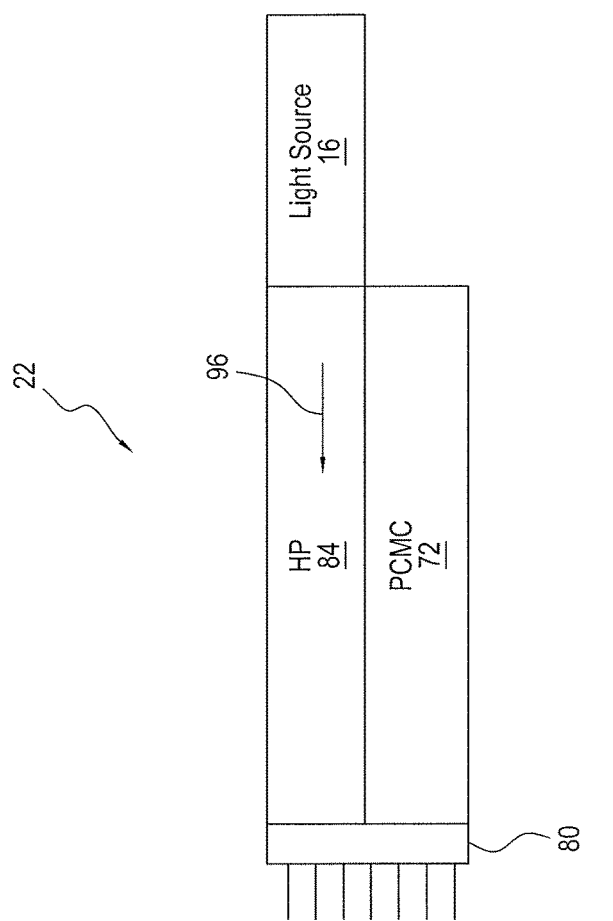
FIG. 8 illustrates a light source thermally connected to a cooling element according to another exemplary embodiment of the present disclosure.

For example, as illustrated in FIG. 8, one or more of the light sources 16 may be thermally, physically, and/or otherwise connected to a heat pipe 84 and/or other like directional thermal conductor known in the art. Such a heat pipe 84 may assist in directionally transferring thermal energy over relatively large distances. For example, one or more heat pipes 84 may be utilized to transmit thermal energy from one or more light sources of the type described herein upwards of, approximately, 24 inches. Such heat pipes 84 may be substantially solid state passive cooling devices having relatively high thermal conductivity characteristics. Accordingly, the one or more heat pipes 84 described herein may be utilized in combination with or in place of the one or more thermal conductors 54, 56 described above. Moreover, exemplary embodiments of the heat pipe 84 may have a greater thermal conductivity in a first direction than in a second direction. Such directional thermal conductivity of the heat pipe 84 may be due to, for example, the molecular structure of the materials utilized to form the heat pipe 84. In addition, the heat flow dynamics of the structures used in constructing the heat pipe 84 may contribute to its directional thermal conductivity characteristics. For example, the heat pipe 84 may comprise two or more substantially concentric tubes enabling recirculation of water, Freon, or other known heat dissipation materials to achieve any desired degree of directional thermal conductivity. As a result, the heat pipe 84 may enable the user to control the direction in which thermal energy flows from the components to which the heat pipe 84 is thermally connected. For example, as shown in FIG. 8, as the light source 16 begins to heat, the heat pipe 84 may draw thermal energy from the light source 16 and transmit it in the direction of arrow 96 to the phase change material component 72. In addition, one or more passive coolers 80, 82 may be thermally connected to the heat pipe 84 and/or the phase change material component 72, and may be configured to assist in dissipating heat therefrom.

The phase change material component 72 described herein may include any phase change material known in the art. Such phase change material may be, for example, a substantially solid wax, oil, or other like substantially organic or inorganic material having a capacity to absorb heat and to change phase once a threshold phase change temperature ($T_{change}$) has been reached. For example, a phase change material having a heat capacity between approximately 100 Joules per gram and approximately 300 Joules per gram may be employed by the exemplary cooling elements 22 described herein. In exemplary embodiments, phase change materials such as Bees Wax with a melting point of approximately 61.8 degrees C. and a latent heat of approximately 177 Joules per gram, and/or N-Octacosane with a melting point of approximately 61.4 degrees C. and a latent heat of approximately 134 Joules per gram may be used. Such materials may facilitate maintaining the one or more light sources thermally connected thereto at a substantially constant operating temperature for a predetermined period of time. For example, as illustrated in FIG. 7, the temperature of the light source 16 may be maintained at approximately $T_{change}$ while the phase change material of the phase change material component 72 completes its phase change. Because such material may change from, for example, solid to liquid, the phase change material component 72 may comprise a substantially enclosed structure configured to safely house liquid phase change material. The phase change material component 72 may comprise a porous sponge-like foam, mesh, grid, honeycomb, or other like structure to assist in retaining such phase change material in both the solid and liquid phase. The phase change material component 72 may also assist in forming a thermally conductive path between the phase change material disposed therein and the heat pipe 84, passive coolers 80, 82, thermal conductors 54, 56, and/or other components of the target marking system 10, 100.

Figure 9:
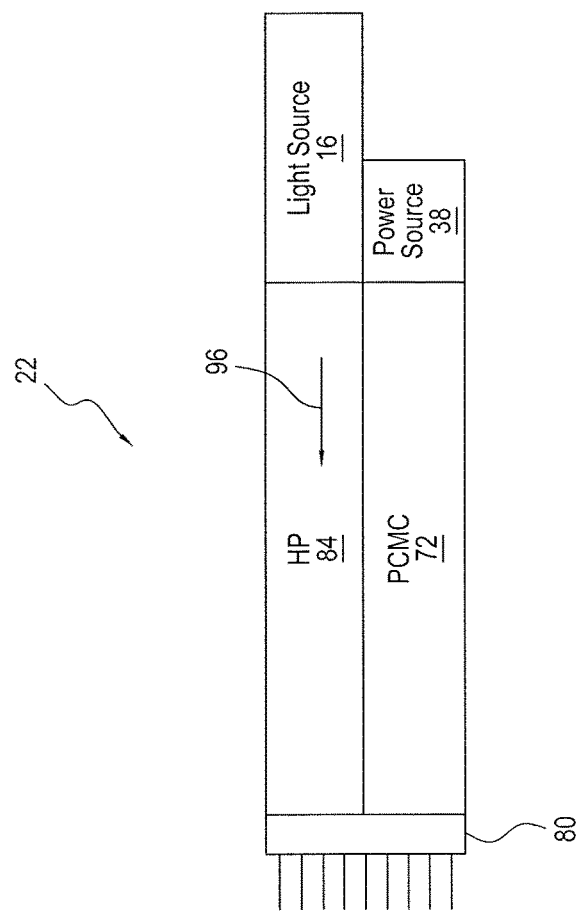
FIG. 9 illustrates a light source thermally connected to a cooling element according to a further exemplary embodiment of the present disclosure.

As described above, extended use of the one or more light sources 16, 18, 19 described herein may drain power from the one or more power sources 38 operably connected thereto. Moreover, such extended use may reduce the thermal energy removal capacity of one or more cooling element components such as, for example, the phase change material component 72. Accordingly, in exemplary embodiments it may be useful to remove and/or replace one or more such cooling element components in conjunction with removal and/or replacement of one or more power source components. In an exemplary embodiment in which the power source 38 comprises one or more removable and/or replaceable batteries, it may be convenient to remove and/or otherwise replace the phase change material component 72 at the same time as such batteries. Accordingly, as shown in FIG. 9, at least one component of the cooling element 22 may be coupled to a removable component of the power source 38. For example, the phase change material component 72 may be coupled to a replaceable battery of the power source 38 such that removal of the replaceable battery results in removal of the phase change material component 72. Because substantially completely draining the stored electrical energy of such a battery will often times coincide with the phase change material within the phase change material component 72 having reached its thermal energy storage limit, replacing both such components at the same time may result in more streamlined operation of the target marking system 10, 100.

Figure 10:
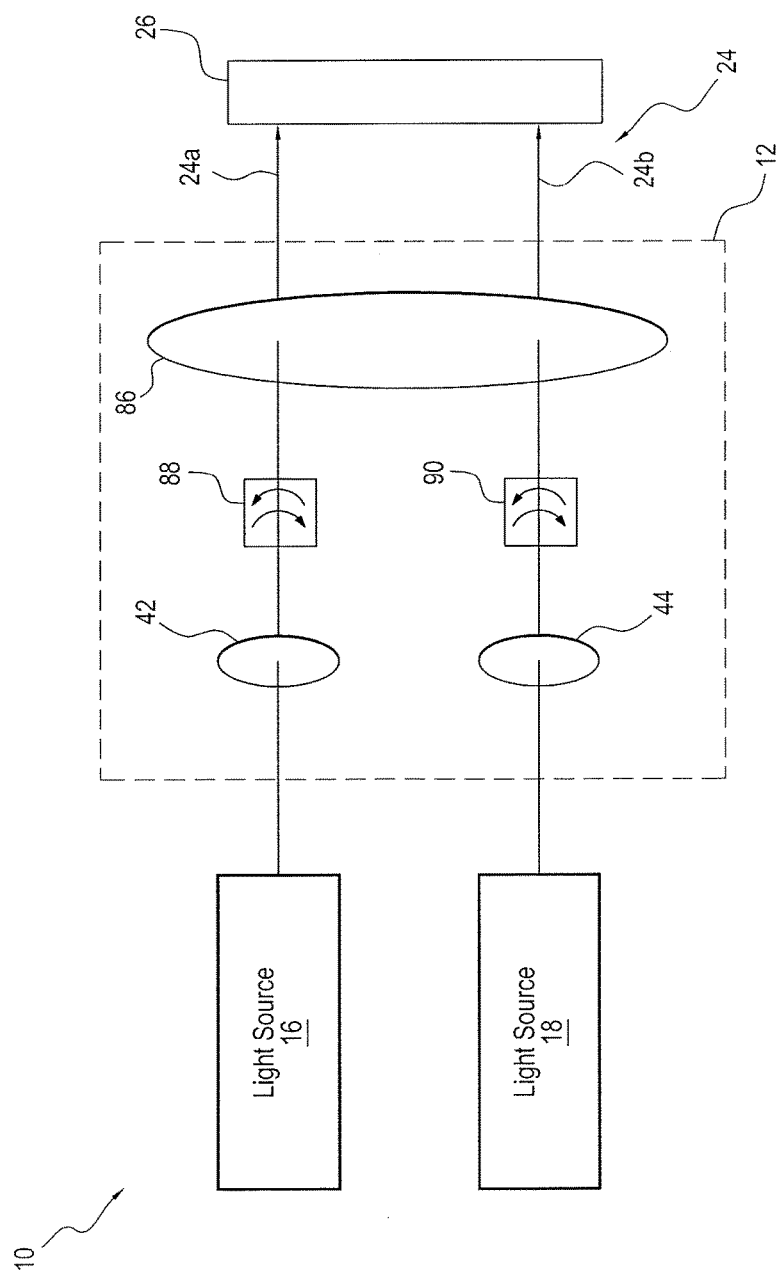
FIG. 10 is a partial schematic of a portion of an exemplary target marking system of the present disclosure.

In another exemplary embodiment of the present disclosure, the optics assembly 12 may include one or more components configured to assist in aligning, for example, the light sources 16, 18, 19 relative to one another. For example, as shown in FIG. 10, the optics assembly 12 may include one or more adjustable alignment windows 88, 90 disposed in the optical path of beams 24*a* and 24*b*, respectively. Such alignment windows 88, 90 may be, for example, any lens, mirror, grating, prism, zero power optic, and/or other known optical component. Such alignment windows 88, 90 may be configured to, for example, manipulate, shift, angle, and/or otherwise change the direction of a collimated beam. For example, each alignment window 88, 90 may be independently tuned, rotated, adjusted, and/or otherwise manipulated by the user of the system 10, 100 to assist in aligning multiple light sources 16, 18, 19 with respect to one another. As shown by the arrows depicted in FIG. 10, in an exemplary embodiment, each of the alignment windows 88, 90 may be rotatable clockwise and counterclockwise to facilitate inter-alignment of the beams 24*a*, 24*b*. Additionally and/or alternatively, alignment windows 88, 90 may be tipped and/or tilted in any desirable direction to facilitate inter-alignment of the beams 24*a*, 24*b*. Such alignment may be performed optically upstream, for example, an additional optic 86 of the optics assembly 12. The optic 86 may be, for example, a zero power optic, a window, a lens, and/or other like optical component useful in directing an emitted beam 24 in the direction of a target 26.

Additional structural components such as, for example, threaded rods, screws, bolts, knobs, thumbscrews, and the like may be utilized to assist in rotating the alignment windows 88, 90 with respect to one another, and with respect to the optic 86. Such additional components may facilitate the fine tuning of the optics assembly 12 as desired. Such tuning components may be accessible on an exterior of the housing 11 (FIG. 1, FIG. 12) such that the user may easily fine tune the optics assembly 12 during and/or prior to use. Such alignment windows 88, 90 may be useful in inter-alignment of the various light sources 16, 18, 19, and may also useful in steering any of the collinear emitted beams 24 described herein. In addition, once each of the windows 88, 90 have been properly positioned for such inter-alignment, the windows 88, 90 may then be aligned and/or otherwise manipulated, in unison, for aligning the collinear emitted beam 24 with, for example, a barrel of the firearm 36 for target aiming purposes. Any of the thumbscrews, knobs, or other additional structural components described above may be utilized for such in unison manipulation.

Figure 11:
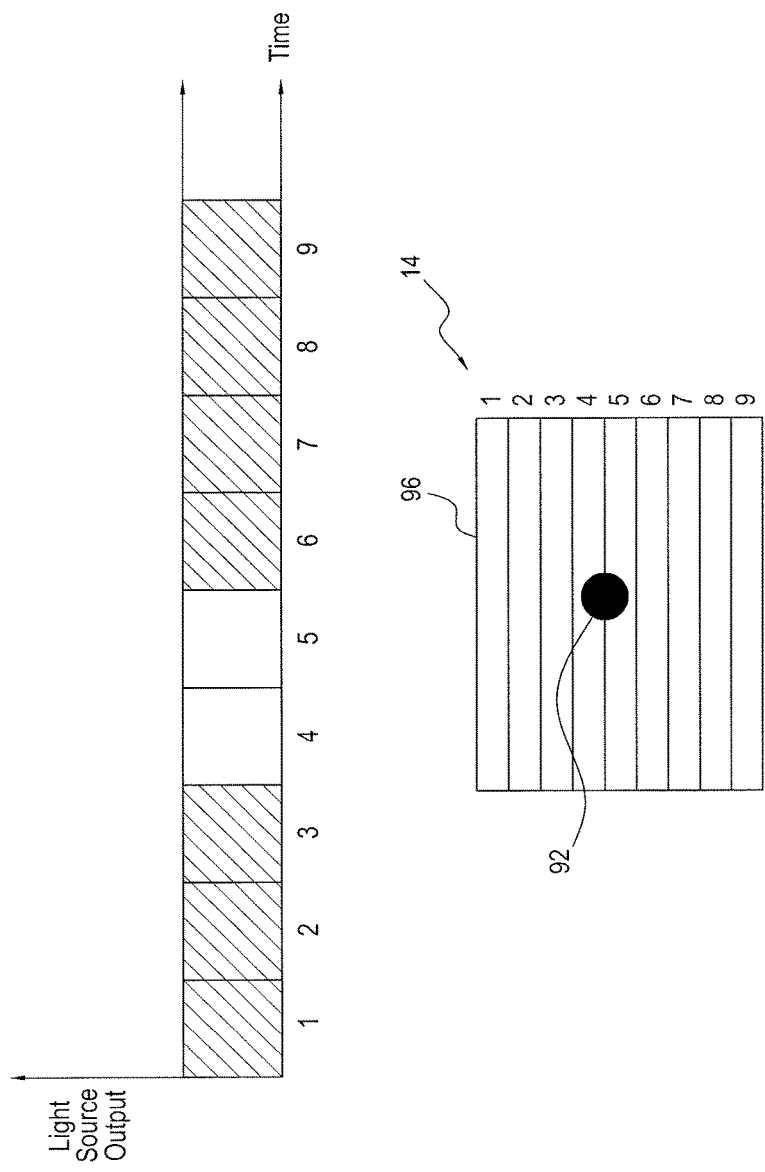
FIG. 11 illustrates an exemplary light source output graph and an exemplary detector according to an embodiment of the present disclosure.

Due to the inefficiencies inherent in many known light sources, and also due to the limitations on available power in hand-held and/or other like target marking systems, it may be advantageous to employ one or more control strategies designed to minimize and/or eliminate unused output or operation of the system components described herein. For example, target marking system users may energize the one or more light sources employed therein substantially constantly. Such substantially constant activation may result in the constant light source output depicted in the graph shown in FIG. 11. Exemplary systems may also control a detector 14 to substantially constantly scan for, for example, re-emitted, reflected, and/or scattered radiation 28, 74, 70 (FIG. 1, FIG. 12). The detector may scan for such radiation on a pixel-by-pixel basis, and such scanning may occur sequentially along, for example, various rows of a pixel array within the detector 14 and/or the display. Such an exemplary array 96 is illustrated in FIG. 11. The array 96 may capture an image of substantially the entire target 26, and the array 96 may image a scene or area that is significantly larger than the area covered by the relatively small diameter emitted beam 24. Thus, although the detector 14 may continuously scan for the radiation 28, 74, 70 sequentially along pixel rows 1-9 illustrated in FIG. 11, the detector 14 may not actually capture, detect, and/or image the area 92 of the target 26 impinged upon by the emitted beam 24 until rows 4 and 5 are scanned. Based on this sequential scanning function of the detector 14, activating the one or more light sources 16, 18, 19 to produce an emitted beam 24 during the time periods where the detector 14 is scanning, for example, pixel rows 1-3 and 6-9 may result in unused light source operation because, even if the emitted beam 24 accurately impinges upon the target 26, the detector 14 will not be scanning pixel rows 4 and 5 during these time periods.

In an exemplary embodiment, one way of reducing the power requirements of the target marking system 10, 100 may be to reduce the duty cycle of the one or more light sources 16, 18, 19 such that the emitted beam 24 is only generated during the time period(s) where the one or more pixel rows corresponding to the area 92 of the target 26 impinged upon by the emitted beam 24. For example, in an exemplary method of controlling the one or more light sources 16, 18, 19 described herein, the light sources may be energized and/or otherwise activated only when the detector 14 is scanning such corresponding pixel rows. As explained above, the light source output graph shown in FIG. 11 illustrates an exemplary embodiment in which a light source 16, 18, 19 is operated throughout the entire scanning time of the detector 14. As indicated by the shaded regions 1-3 and 6-9, the energy expended in producing an emitted beam 24 during these time periods may be substantially unused since the detector 14 is only able to image the area 92 when scanning in pixel rows 4 and 5. By triggering, synching, phase locking, and/or otherwise keying the activation of the light source 16, 18, 19 to the scanning cycle of the detector 14, the user may be able to substantially reduce the operating time of the light sources 16, 18, 19. Such reduced operating time may result in a corresponding reduction in thermal energy generation and power consumption. As a result, such a control strategy may reduce the demands on cooling element 22 and on power source 38, and may greatly enhance the operability of the system 10, 100.

In addition to the control methods discussed above, the controller 20, power source 38 and/or other components of the system 10, 100 described herein may be programmed, operated, controlled, and/or otherwise employed to provide any desired voltage to the one or more light sources 16, 18, 19. Such components may utilize any of a variety of control circuits and/or topographies to facilitate such control. For example, the systems 10, 100 described herein may provide a substantially constant current and/or substantially constant input power to the one or more light sources 16, 18, 19. Alternatively and/or in addition, the controller 20 may control the light sources utilizing any known feedback loop, and may drive the respective light sources to produce a substantially constant output power. Such a drive control strategy would require use of suitable sensors and/or other known feedback loop control components. In still another exemplary embodiment, the one or more light sources 16, 18, 19 may be driven in order to maintain a substantially constant laser temperature. In such an exemplary embodiment, one or more temperature sensors may be employed in a feedback loop employed by the controller 20.

It is further understood that the systems 10, 100 described herein may utilize any type of switched mode power supply, voltage regulation, and/or other circuit topography known in the art. Such circuit topographies may include isolated converters and/or non-isolated converters. For example, the controller 20, power source 38, and/or other components of the systems 10, 100 may include a drive circuit configured to supply voltage to the one or more light sources 16, 18, 19. Such a drive circuit may include one or more non-isolated converters such as buck converters, boost converters, buck-boost converters, split-pi converters, Ćuk converters, single-ended primary inductor converters, Zeta converters, and/or charge pump converters. Alternatively, and/or in addition, such a drive circuit may include one or more isolated converter circuits, and such circuits may include one or more transformers configured to produce a higher or lower voltage than that inputted to the transformer. Such isolated converters may include, for example, SIPEX converter, an inverting converter, a fly-back converter, a ringing choke converter, a half-forward converter, a forward converter, a resonate forward converter, a push-pull converter, a half-bridge converter, a full-bridge converter, a resonate zero voltage switched converter, and/or an isolated Ćuk converter. Any or all of the above converter circuit typographies may be utilized with and/or otherwise employed by the constant current, constant input power, constant output power, or constant temperature control schemes described above.

Figure 13:
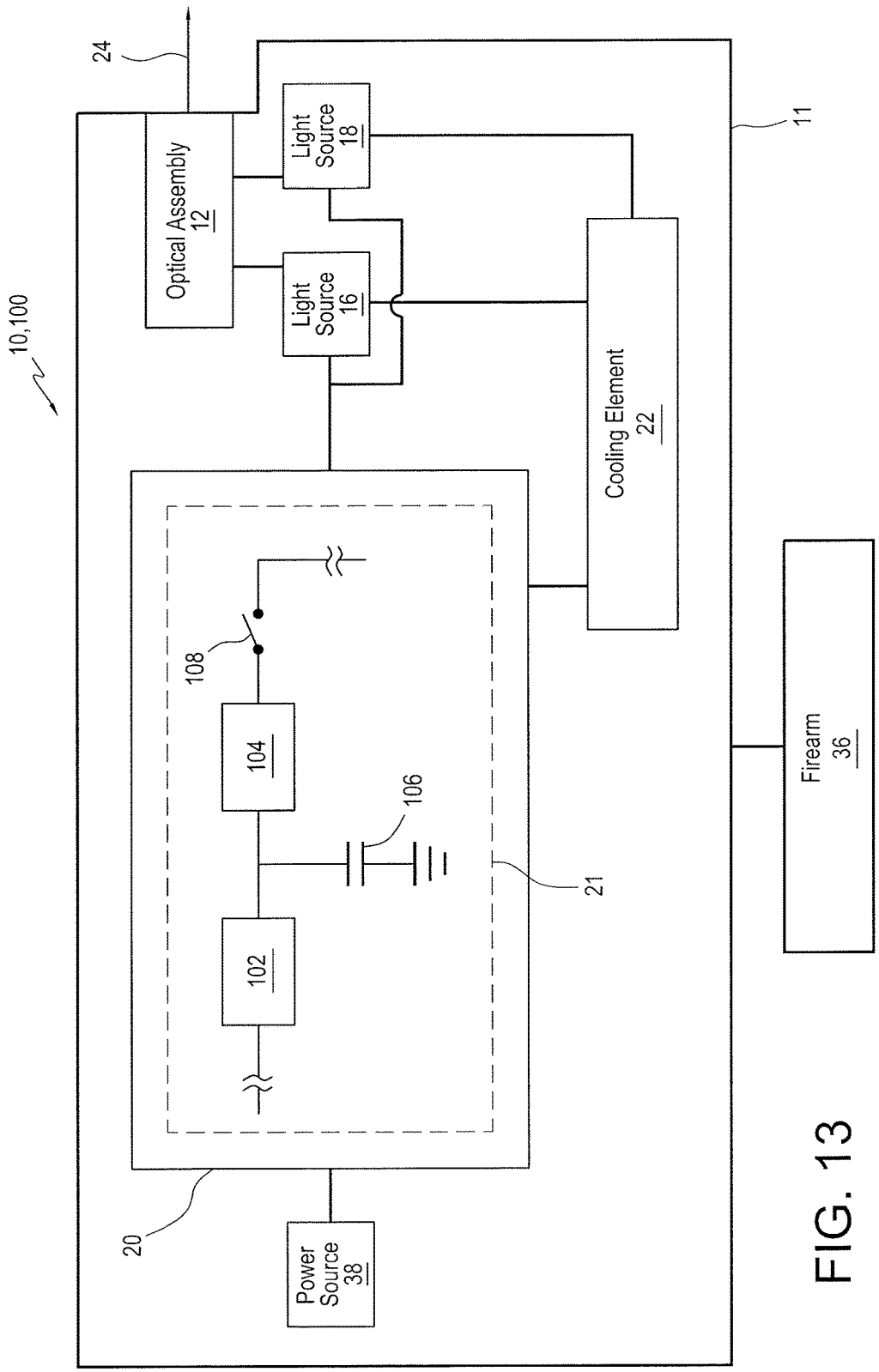
FIG. 13 illustrates an exemplary drive circuit for use with a target marking system of the present disclosure.

For example, as shown in FIG. 13, a drive circuit 21 of the controller 20 may include a first converter 102 connected in series with a second converter 104, and a capacitor 106 connected between the first and second converters 102, 104. The detector 14, display 60 and other components of the exemplary target marking system 10, 100 described above have been omitted from FIG. 13 for ease of description.

The first and second converters 102, 104 may be the same type of electrical converter or, alternatively, the converters 102, 104 may be different types of electrical converters. For example, one or both of the first and second converters 102, 104 may comprise any of the isolated or non-isolated converters described above. In an exemplary embodiment, the first converter 102 may be configured to charge the capacitor 106 and/or maintain a voltage of the capacitor 106 between approximately 2 volts and approximately 8 volts while the one or more light sources 16, 18 emits the beam 24. In an exemplary embodiment, the first converter 102 may assist in charging the capacitor 106 to approximately 5 volts before the beam 24 is emitted. In order to maintain such desired voltage levels in the capacitor 106 before and/or while the beam 24 is emitted, the first converter 102 may comprise a buck converter if the voltage of the power source 38 is greater than the voltage stored in the capacitor 106. Alternatively, in order to maintain such voltage levels in the capacitor 106 the first converter 102 may comprise a boost converter if the voltage of the power source 38 is less than the voltage stored in the capacitor 106. In still another exemplary embodiment, the first converter 102 may comprise a buck-boost converter in applications in which the voltage of the power source 38 may be greater than or less than the voltage stored in the capacitor 106.

In any of the embodiments described herein, the first converter 102 may be configured to draw a substantially constant current from the power source 38 while the one or more light sources 16, 18 emits the beam 24. The first converter 102 may be configured to direct such a substantially constant current from the power source 38 to the capacitor 106. By directing such a constant current to the capacitor 106, the first converter 102 may assist in maintaining the capacitor 106 at a substantially constant voltage, such as a voltage between approximately 2 volts and approximately 8 volts, as described above. It is understood, however, that as the beam 24 is emitted, the capacitor 106 may discharge at least a portion of the stored voltage. For example, the capacitor 106 may discharge approximately ⅔ of the stored voltage during each pulse of the emitted beam 24. The amount of stored voltage that is discharged by the capacitor 106 may depend upon, for example, the pulse width of the beam 24, the output power of the beam 24, and/or other characteristics of the beam 24 and/or the light sources 16, 18. The capacitor 106 may be any type of capacitor and/or inductor known in the art, and in an exemplary embodiment, the capacitor 106 may comprise a single 0.15 farad capacitor having a capacity of at least approximately 5 volts.

The second converter 104 may comprise any of the above converter types, and the second converter 104 may be configured to convert the voltage and/or energy stored in the capacitor 106 to a desired voltage useful in driving the one or more light sources 16, 18. It is understood that in exemplary embodiments in which one of the light sources 16, 18 comprises an IR semiconductor laser, such a corresponding desired voltage may be between approximately 1.5 volts and approximately 2.5 volts. In additional exemplary embodiments in which one of the light sources 16, 18 comprises a QCL, such a corresponding desired voltage may be between approximately 12 volts and approximately 14 volts. In an exemplary embodiment, the second converter 104 may be selectively enabled and/or disabled to pulse the beam 24 emitted by the one or more light sources 16, 18. In still further exemplary embodiments, the second converter 104 may be controlled in response to, for example, an output power of the beam 24, and/or in response to an operating characteristic of one or more of the target marking system components. In such an exemplary embodiment, the second converter 104 may maintain the output power of the beam 24 substantially constant. For example, the second converter 104 may assist in maintaining an output power of each pulse of a pulsed emitted beam 24 substantially constant, and the operation of the second converter 104 may be controlled in response to the output power of each pulse of the pulsed beam 24. Such a control strategy may be open-loop or closed-loop in nature.

The drive circuit 21 may further comprise one or more switches 108 connected in series with the one or more light sources 16, 18 to facilitate pulsing of the beam 24. Such switches 108 may comprise, for example, a MOSFET switch and/or any other like switching device. In exemplary embodiments in which the drive circuit 21 comprises a switch 108, it is understood that the second converter 104 may be substantially continuously enabled during operation and the switch 108 may be selectively controlled to pulse the beam 24. Alternatively, the switch 108 may be omitted, and the beam 24 may be pulsed using the second converter 104 and/or other components of the drive circuit 21 and/or the controller 20.

The exemplary drive circuit 21 illustrated in FIG. 13, and the variations described above, represents an improvement over current less efficient laser drive circuit designs. For example, typical battery-powered laser drive circuits may employ a standard 1.5 F capacitor in parallel with one or more batteries to supply energy to a laser. However, due to the amount of energy typically required by semiconductor lasers (such as QCLs) per pulse, standard low-capacity capacitors are not suited for such applications.

In other known battery-powered laser drive circuits, a standard 1.5 F capacitor may be disposed in series between a converter and the laser. However, since such capacitors are typically rated for approximately 2.7 volts and the typical semiconductor laser requires at least approximately 12 volts for operation, such capacitors are not capable of providing the proper operating voltage to the laser. Although some circuits may employ several such capacitors in series, between the converter and the laser, to store sufficient energy for pulsing and/or otherwise operating the laser, such circuit configurations are plagued by unacceptable startup delays associated with charging the multiple capacitors. Moreover, the known drive circuits described above lack efficiency during use since the amount of energy drawn from such standard 1.5 F capacitors (approximately 1.25 Joules per pulse for typical semiconductor lasers) is small relative to the amount of energy stored in the capacitor when fully charged (approximately 18 joules total).

The exemplary drive circuits 21 described herein, on the other hand, overcome the deficiencies of known semiconductor laser drive circuits and facilitate supplying tens of watts of peak power to such lasers while making efficient use of the limited energy stored in the portable power source 38. Such drive circuits 21 are well suited for the handheld and/or otherwise portable target marking systems 10, 100 of the present disclosure, and such drive circuits may be tuned to operate the one or more light sources 16, 18 to emit a beam 24 having a pulse width in the range of approximately 25 ms to approximately 100 ms, an average power between approximately 2 Watts and approximately 3 Watts, a peak power of at least 25 Watts, and a pulse rate between approximately 1 Hz and approximately 3 Hz.

The invention has been described in detail with particular reference to a presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

The invention claimed is:

1. A system, comprising:
   a handheld housing;
   a light source disposed within the housing; and
   an optics assembly configured to form a divergent emitted beam exiting the housing, the emitted beam being formed with radiation received from the light source and comprising:
      first radiation emitted by the light source, the first radiation being limited to a first wavelength band, and
      second radiation emitted by the light source, the second radiation being limited to a second wavelength band different from the first wavelength band.

2. The system of claim 1, wherein the second radiation band is spaced from the first wavelength band.

3. The system of claim 1, wherein:
   the light source comprises a first light source,
   the system further comprises a second light source disposed within the housing, and
   the second radiation is emitted by the second light source.

4. The system of claim 1, wherein the first wavelength band includes wavelengths between approximately 0.9 μm and approximately 2.5 μm.

5. The system of claim 1, wherein the first wavelength band includes wavelengths between approximately 2 μm and approximately 5 μm, and the second wavelength band includes wavelengths between approximately 8 μm and approximately 30 μm.

6. The system of claim 1, further comprising a controller operably connected to the light source, the controller being configured to:
   operate the light source in at least one of a first duty cycle, or a second duty cycle different from the first duty cycle; and
   cause the light source to emit the first radiation with a desired frequency signature.

7. The system of claim 6, wherein the controller is configured to enable a user of the system to modify at least one of a frequency of the emitted beam, or a pulse pattern of the emitted beam.

8. The system of claim 1, wherein the housing is substantially fluid-tight, and at least part of the optics assembly is disposed within the housing.

9. The system of claim 1, wherein the light source comprises a first light source, the system further comprising:
   a second light source disposed within the housing and configured to emit the second radiation; and
   a selection device configured to enable a user of the system to select at least one of the first light source or the second light source for activation.

10. The system of claim 9, further comprising an activation device configured to enable the user to activate the at least one of the first light source or the second light source.

11. The system of claim 1, further comprising an active cooling element disposed in thermal contact with the light source.

12. A system, comprising:
    a handheld housing;
    a first light source disposed within the housing and configured to emit first radiation within a single first wavelength band, the first wavelength band consisting of one of the short wavelength infrared band, the mid-wave infrared band, or the long-wave infrared band;
    a second light source disposed within the housing and configured to emit second radiation within a second wavelength band different from the first wavelength band; and
    an optics assembly configured to form a divergent emitted beam from the first radiation and the second radiation, the emitted beam being characterized by the first wavelength band and the second wavelength band.

13. The system of claim 12, wherein the optics assembly comprises an adjustment window that enables manual alignment of the first radiation relative to the second radiation.

14. The system of claim 12, wherein the first radiation has a first polarization, and the second radiation has a second polarization different from the first polarization.

15. The system of claim 12, wherein a wavelength of the first radiation is between approximately 2 μm and approximately 5 μm, and a wavelength of the second radiation is between approximately 8 μm and approximately 30 μm, the system further comprising:
    a controller operably connected to the first light source and the second light source, the controller being configured to enable a user of the system to modify at least one of a frequency of the emitted beam, or a pulse pattern of the emitted beam.

16. The system of claim 12, wherein the optics system comprises a wavelength beam combiner disposed optically downstream from a collimating lens.

17. The system of claim 12, wherein the optics system comprises a diffraction grating disposed optically downstream from a collimating lens, the diffraction grating combining the first radiation and the second radiation to form the emitted beam.

18. A method, comprising:
controlling a first light source to direct first radiation to an optics assembly, the first light source being disposed within a handheld housing, and the first radiation being within a single first wavelength band, the first wavelength band consisting of one of the short wavelength infrared band, the mid-wave infrared band, or the long-wave infrared band;
controlling a second light source disposed within the housing to direct second radiation to the optics assembly, the second radiation being within a second wavelength band different from the first wavelength band; and
forming, with the optics assembly, a divergent emitted beam from the first radiation and the second radiation, the emitted beam being characterized by the first wavelength band and the second wavelength band.

19. The method of claim 18, wherein a wavelength of the first radiation is between approximately 2 μm and approximately 5 μm, and a wavelength of the second radiation is between approximately 8 μm and approximately 30 μm.

20. The method of claim 18, further comprising modifying at least one of a frequency of the emitted beam, or a pulse pattern of the emitted beam.

* * * * *